(12) United States Patent
Dunn et al.

(10) Patent No.: US 9,835,586 B2
(45) Date of Patent: Dec. 5, 2017

(54) PORTABLE ELECTROCHEMICAL CELL WITH TEMPERATURE CONTROL AND SURFACE MORPHOLOGY INDEPENDENCE

(75) Inventors: Ryan C. Dunn, Charlottesville, VA (US); Guy D. Davis, Catonsville, MD (US); Robert A. Ross, Charlottesville, VA (US); Paul A. Bell, Catonsville, MD (US)

(73) Assignee: ELECTRAWATCH, INC., Charlottesville, VA (US)

( * ) Notice: Subject to any disclaimer, the term of this patent is extended or adjusted under 35 U.S.C. 154(b) by 569 days.

(21) Appl. No.: 13/561,032

(22) Filed: Jul. 28, 2012

(65) Prior Publication Data

US 2013/0186756 A1    Jul. 25, 2013

Related U.S. Application Data

(63) Continuation-in-part of application No. PCT/US2011/022286, filed on Jan. 24, 2011.

(60) Provisional application No. 61/297,947, filed on Jan. 25, 2010.

(51) Int. Cl.
  *G01N 27/416*  (2006.01)
  *G01N 17/02*   (2006.01)
(52) U.S. Cl.
  CPC ......... *G01N 27/416* (2013.01); *G01N 17/02* (2013.01)
(58) Field of Classification Search
  CPC .... G01N 17/02; G01N 17/04; G01N 27/4163; G01N 27/42; G01N 27/423; G01N 33/38–33/42; F16C 29/00–29/008

USPC ............... 204/404, 298.05; 205/775.5–777
See application file for complete search history.

(56) References Cited

U.S. PATENT DOCUMENTS

| 4,861,453 | A | * | 8/1989 | Matsuoka et al. ............ 204/404 |
| 4,962,360 | A | * | 10/1990 | Homma et al. ............... 324/700 |
| 2007/0079662 | A1 | * | 4/2007 | Engelbart ............ G01B 5/0004 73/866.5 |
| 2009/0027070 | A1 | * | 1/2009 | Gelling ................. G01N 17/02 324/693 |

* cited by examiner

*Primary Examiner* — J. Christopher Ball
(74) *Attorney, Agent, or Firm* — Paul A. Bell

(57) ABSTRACT

The invention comprises portable, rugged and relatively compact electrochemical cells. Each may be removably and nondestructively secured to one surface of a substrate of indefinite size. In-situ electrochemical measurements may be made on portions of existing structures such as ships, bridges, or buildings. An electrochemical cell is disclosed which comprises an analytical chamber which can be utilized with either on-board or external potentiostats. The electrochemical cell has a mounting means which permits the cell to be secured to substrates with irregular surface morphology and to horizontal, vertical or intermediately oriented surfaces. The electrochemical cell provides a means to control the temperature of the electrolyte and the substrate area of interest to permit more accurate and consistent elecrochemical measurements. Said probe is capable of performing electrochemical measurements such as a monitoring corrosion, effectiveness, or integrity of conductive and nonconductive coatings on bare and coated metallic or conductive substrates.

22 Claims, 27 Drawing Sheets

PORTABLE ELECTROCHEMICAL CELL WITH TEMPERATURE CONTROL AND SURFACE MORPHOLOGY INDEPENDENCE

CROSS-REFERENCE TO RELATED APPLICATIONS

This application claims the benefit of U.S. Provisional Application 61/297,947, filed on Jan. 25, 2010. This application is also a Continuation-In-Part of U.S. patent application Ser. No. 13/522,524 filed on Jan. 24, 2011 as International Patent Application PCT/US2011/022286.

STATEMENT REGARDING FEDERALLY SPONSORED RESEARCH OR DEVELOPMENT

This invention was made with government support under N00178-07-D-4078 DO EHP7 awarded by United States Navy. The government has certain rights in the invention. Per 48 CFR 52.227-11(b) the Federal Government shall have a nonexclusive, nontransferable, irrevocable, paid-up license.

SEQUENCE LISTING

Not Applicable

BACKGROUND OF THE INVENTION

The invention comprises six different but related types of electrochemical cell. The six electrochemical cells of the invention share several important common features.

In the first instance, they are all portable. That is, they can each be used in the field, e.g. outside the laboratory. They can be moved to any desired location to make electrochemical measurements on a wide variety of different sized and shaped substrates. Obviously, even though the electrochemical cells of the invention are designed to be usable outside the laboratory, they will work just as well in the laboratory, if desired.

Secondly, each electrochemical cell has the ability to be removably and nondestructively secured to one surface of a substrate of indefinite size. This feature derives from the attachment means used with each electrochemical cell of the invention. Removable and nondestructive attachment is defined herein to mean that the electrochemical cells of the invention may be attached and then easily removed from the substrate with no damage at all to the electrochemical cell and with only minimal damage to the substrate. For example, the substrate may require a small amount of cleaning because of spilled electrolyte. In addition, certain types of electrochemical measurements may require any coating of the substrate to be removed prior to taking the measurements. Obviously, this coating would have to be replaced in order to return the substrate to its original condition.

The attachment means permits the cells to be used to make electrochemical measurements on substrates of widely varying sizes and shapes. Since the attachment means will secure the electrochemical cells of the invention to substrates of widely varying sizes, in-situ electrochemical measurements may be made on portions of existing structures which may be quite large—for example ships, bridges, or buildings.

Prior art electrochemical cells typically are limited to making measurements on relatively small sized substrates, capable of being inserted into the cell interior. Some prior art cells have the ability to make measurements on larger substrates but require access to an edge of the substrate. Thus, most all of the prior art electrochemical cells are severely limited as to the size of the substrates they can work with.

Lastly, they are all relatively compact and rugged compared to existing electrochemical cells. For example, glass is often used in the construction of the prior art electrochemical cells and, for obvious reasons, a glass electrochemical cell cannot fairly be characterized as being "rugged". The electrochemical cells of the invention are made primarily of modern polymeric materials which are much more rugged than glass.

The first and most basic electrochemical cell comprises an analytical chamber which can be utilized with existing prior art potentiostats. This chamber has means to contain the necessary electrolyte and means to secure a counter electrode and a reference electrode therein. The chamber also has an adjustable attachment means to permit the chamber to be removably and nondestructively attached to and then removed from the surface of a substrate of indefinite size.

The second electrochemical cell is a compact, rugged self-contained portable probe comprising an electrochemical cell and potentiostat to perform electrochemical measurements. The probe of the invention is particularly useful to monitor corrosion on bare and coated substrates. The probe of the invention is designed to work on metals and other conductive substrates. It is also designed to determine the effectiveness or integrity of conductive and nonconductive coatings on conductive substrates.

The third electrochemical cell is a modification of the second cell which retains the self-contained electronics component of the second electrochemical cell, but eliminates the fluidics handling portion of the second embodiment.

The fourth electrochemical cell is a modification of the first three cells which allows for more adjustment of the attachment means to permit the cell to be secured to substrates with irregular surface morphology, e.g. substrates which are not planar or have an irregular surface.

The fifth electrochemical cell is a modification of the third cell which retains the self-contained electronics component of the second embodiment and eliminates the fluidics handling portion of the second embodiment. In addition, the fifth electrochemical cell permits accurate temperature control of the electrolyte and of the local substrate area where the electrochemical measurements are being made. This cell also has an attachments means which permits the cell to be secured to substrates with a somewhat irregular surface morphology.

The sixth electrochemical cell is a modification of the fifth cell which eliminates the self-contained electronics component.

Corrosion is a wide-spread problem that affects nearly all industry and government sectors. A recent report determined that the direct cost of corrosion in the United States to be 3.1% of the Gross Domestic product (GDP) [G. H. Koch, et al. "Corrosion Costs and Preventive Strategies in the United States," Report by CC Technologies Laboratories, Inc. to Federal Highway Administration (FHWA), Office of Infrastructure Research and Development, Report FHWA-RD-01-156, September 2001]. This corresponds to $300B annually or $1000 per person. This figure includes only the direct costs (e.g., corrosion prevention, corrosion inspection, and replacement or refurbishment of corroded structures). The indirect costs (e.g., lost productivity, taxes, and overhead) were conservatively estimated to be equal to the direct costs.

Thus, there is a pressing need to determine or monitor the susceptibility or rate of corrosion of critical structures and components in the field. Because corrosion is an electrochemical process, electrochemical measurements are the most effective means to determine if a material is corroding, is susceptible to corrosion, or is protected from corrosion. These measurements are generally acquired by placing the material being studied (the working electrode) in a liquid electrolyte along with reference and counter electrodes to form an electrochemical cell and using a potentiostat (a controlled power supply with a sensitive zero-resistance ammeter (ZRA) or other galvanometer) to apply a potential or voltage between the reference electrode and the material being studied and measuring the current induced between the material and the counter electrode. The potential can be constant or varying and it and the current can be either DC or AC. The relationship of the current to the potential or the impedance (potential divided by current for ac measurements) allows one skilled in the art to determine whether the material is corroding, susceptible to corrosion or protected from corrosion and if a coating is protective or not. The potentiostats are generally relatively large and heavy bench instruments that require standard electrical power. An example of a prior art potentiostat would be the Gamry Reference 3000 potentiostat that is approximately 20-cm× 23-cm×30-cm and weighs approximately 6 kg.

In the procedure described above, the material or specimen must be relatively small with dimensions in inches or centimeters to allow the specimen to be immersed in a beaker or other container filled with a suitable electrolyte. For larger specimens or structures that are too large to immerse completely in an electrolyte, electrochemical measurements can sometimes be acquired if the desired area of the structure is horizontal or nearly horizontal by placing a bottomless cylinder (or similar construction) on the structure and sealing it to the structure with an o-ring, gasket, sealant, or other means so that the structure becomes the bottom of the container. Other configurations allow the material to be vertical and form the side of a horizontal cylinder with openings along the top of the cylinder to allow the electrolyte and electrodes to be added. The container is then filled with the appropriate electrolyte and counter and reference electrodes immersed into the electrolyte. A potentiostat is connected to the structures and the electrodes and the electrochemical measurements acquired. Once the measurements are completed, the setup must be reversed with the counter and reference electrodes removed and stored, the electrolyte drained and stored or disposed of, the bottomless cylinder removed, and the structure cleaned of any sealant. Examples of this type of apparatus include the Gamry Instruments PTC1 Paint Test Cell, the Princeton Applied Research Tait Cell K0307, and the Princeton Applied Research Flat Cell K0235. The PTC1 Paint Test Cell and the Flat Cell K0235 require the specimen to be clamped to the open end of the container and thus limit the size and configuration of specimens capable to be studied. The Tait Cell holds the specimen via threaded rods and a backing plate. It could be attached to a large structure provided that holes were drilled into the structure—a practice that is rarely allowed. All require a separate (large) potentiostat to be connected to the electrodes and specimen.

An analysis detected a number of documents of interest related to these patents and to the present invention. Table 1 identifies these patents.

TABLE 1

| Pat. | Title | Inventor |
|---|---|---|
| U.S. Pat. No. 7,265,559 | Self-calibrating corrosion measurement field device with improved signal measurement and excitation circuitry | Hladky, K. et al. |
| U.S. Pat. No. 7,245,132 | Intrinsically safe corrosion measurement and history logging field device | Poirier, D. M. et al. |
| U.S. Pat. No. 7,239,156 | Configurable corrosion measurement field device | Hladky, K et al. |
| U.S. Pat. No. 7,180,309 | Electronic system for multielectrode sensors and electrochemical devices | Yang, X. S. |
| U.S. Pat. No. 7,148,706 | Embeddable corrosion rate meters for remote monitoring of structures susceptible to corrosion | Srinivasan, R. et al. |
| U.S. Pat. No. 7,397,370 | Monitoring an environment using a RFID assembly | Bratkovski, A |
| US20060144719 | Quantitative, real time measurements of localized corrosion events | Gill, R. P. et al |
| U.S. Pat. No. 7,034,660 | Sensor devices for structural health monitoring | Watters, D. G. et al. |
| U.S. Pat. No. 6,776,889 | Corrosion monitoring | Atherton, E. |
| U.S. Pat. No. 6,683,463 | Sensor array for electrochemical corrosion monitoring | Yang, L. et al. |
| U.S. Pat. No. 6,611,151 | Coating assessment system based on electrochemical noise | Ruedisueli, R. L. et al. |
| U.S. Pat. No. 6,320,395 | Apparatus and method for electrochemical corrosion monitoring | Bosch, R.-W et al. |
| U.S. Pat. No. 6,294,074 | Electrode design for corrosion monitoring using electrochemical noise measurements | Lin, Y. P. J. et al,. |
| U.S. Pat. No. 6,280,603 | Electrochemical noise technique for corrosion | Jovancicevic, V. |
| US20050122121 | Direct Resistance Measurement Corrosion Probe | Gilboe, D. |

These patents involve a variety of different means to detect corrosion or the corrosivity of the environment, including fiber optic measurements, strain gauges, electrical resistance, electrochemical noise, current between two electrodes, and degradation of witness material. Some are valid only for metal surfaces; others only for painted surfaces. None include a self-contained electrochemical cell that directly measures electrochemical properties of the structure of interest, stores the results, and transfers them to a portable computer or similar device.

SUMMARY OF THE INVENTION

The first and most basic electrochemical cell comprises an analytical chamber which can be utilized with existing prior art potentiostats. This chamber has means to contain the necessary electrolyte and means to secure a counter electrode and a reference electrode therein. The chamber also has an adjustable attachment means to permit the chamber to be attached to and then removed from the surface of a substrate of indefinite size. The attachment means allows for nondestructive attachment and removal from a substrate and does not require access to an edge of the substrate to provide the necessary attachment. This feature allows for in-situ electrochemical measurements on portions of existing structures which may be quite large—for example, ships, bridges or buildings.

The second embodiment of the invention comprises a self-contained portable electrochemical cell and potentiostat probe which simplifies the steps of determining or monitoring the susceptibility or rate of corrosion of critical structures and components in the field. The probe comprises three components: 1) a miniature potentiostat; 2) a self-contained electrochemical cell; and 3) a means to firmly attach the apparatus to the structure.

The electrochemical cell comprises an electrolyte reservoir, a measurement or analytical compartment that is sealed to the substrate of interest via an o-ring or similar sealing means, counter and reference electrodes located in the measurement or analytical compartment, a means to make electrical contact to the structure, and the pump, valves and tubing necessary to transport the electrolyte from the reservoir to the measurement or analytical compartment and the reverse.

The probe is suitable for large and small structures and can be attached nondestructively. Measurements can be acquired in the field or in the laboratory.

The third embodiment of the invention is a modification of the second embodiment which retains the miniature potentiostat but does away with the fluid handling portions of the second embodiment electrochemical cell.

The fourth embodiment of the invention is a modification of the first embodiment which allows for more adjustment of the attachment means to permit the cell to be secured to substrates with irregular surface morphology, e.g. substrates which are not planar or have an irregular surface.

The fifth embodiment of the invention is a modification of the third embodiment which retains the self-contained electronics component of the second embodiment and eliminates the fluidics handling portion of the second embodiment. In addition, the fifth electrochemical cell permits accurate temperature control of the electrolyte and of the local substrate area where the electrochemical measurements are being made. This cell also has an attachments means which permits the cell to be secured to substrates with a somewhat irregular surface morphology.

The sixth embodiment of the invention is a modification of the fifth embodiment which eliminates the self-contained electronics component and is designed to be used with an external potentiostat.

DETAILED DESCRIPTION

It should be understood that the terms "voltage" and "potential" are used interchangeably herein and mean the same thing.

Figure 1:
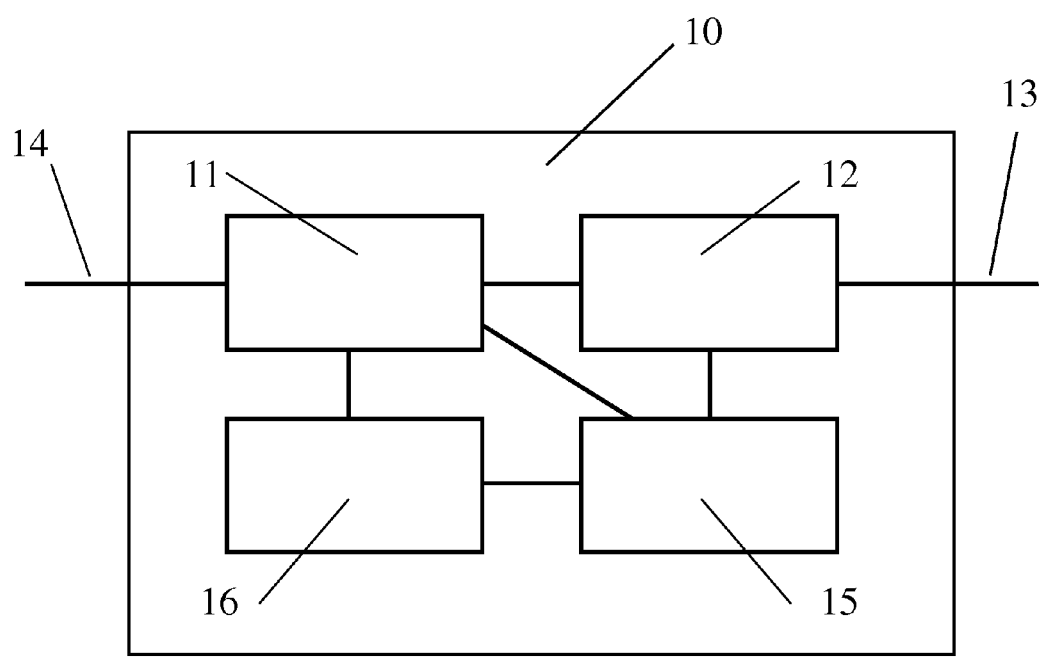
FIG. 1 shows a block diagram of a generic prior art potentiostat.

FIG. 1 shows a block diagram of a generic prior art potentiostat 10 comprising of a voltage/current generator 11; a electrometer 12 to measure the current induced by applied voltage or to measure the voltage induced by applied current; a means 13 to make electrical connection to the specimen being measured; a means 14 to make electrical connection to reference and counter electrodes immersed into an electrolyte along with the specimen; a means 15 to convert the measurement into an electrochemical impedance measurement; and a means for input/output 16.

Figure 2:
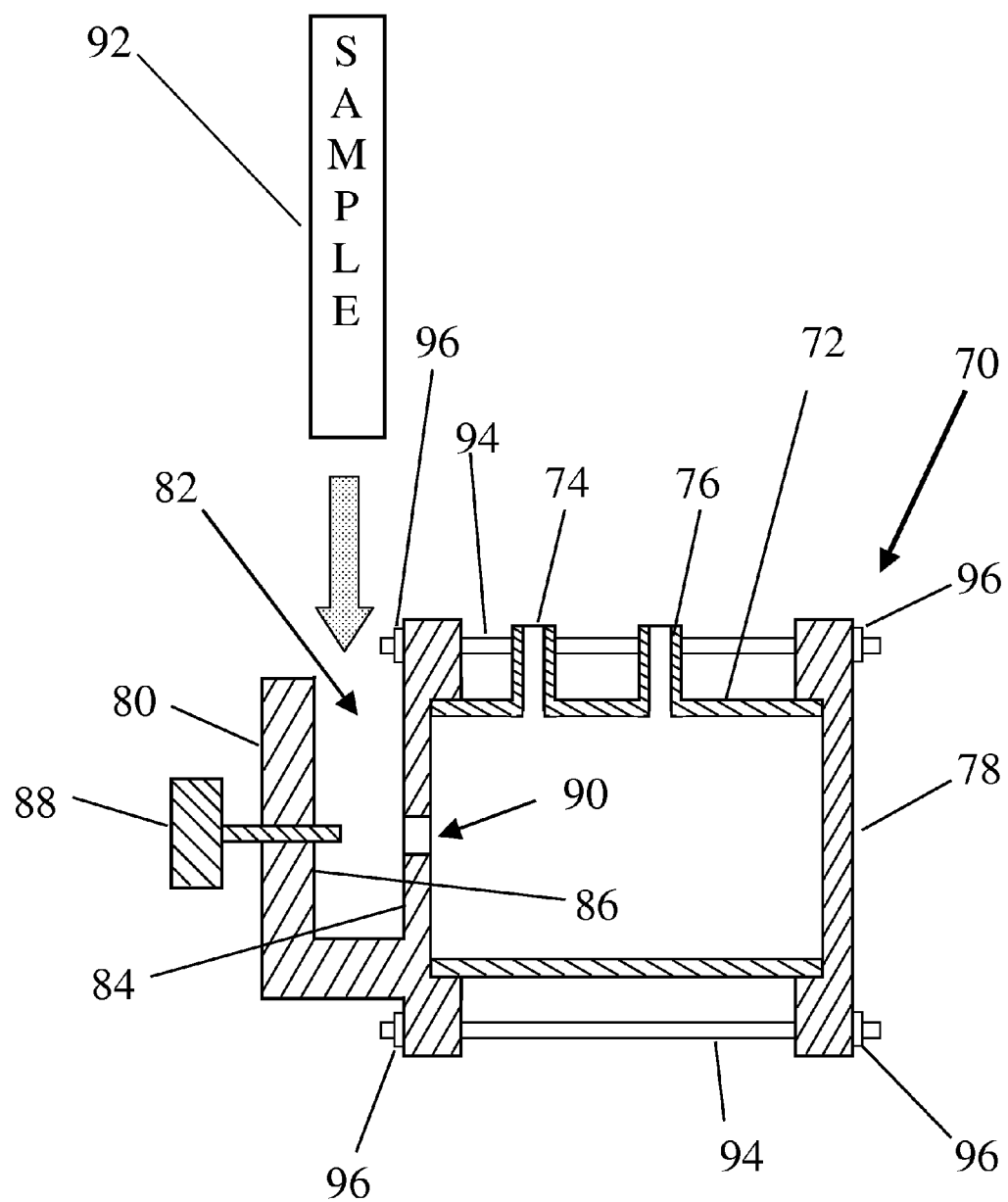
FIG. 2 shows a prior art electrochemical cell which works with an edge of a sample.

FIG. 2 shows a prior art electrochemical cell that is designed to grip a sample specimen at an edge thereof. Most prior art electrochemical cells are designed to make electrochemical measurements on small size samples or on samples which allow for the cell to be secured to one edge thereof.

In the first situation, the substrate of interest has to be small enough to fit within the electrochemical cell. If the substrate of interest is not small enough to fit within the electrochemical cell, the substrate would have to be partially destroyed by physically removing a suitably sized sample coupon. This sample coupon is then inserted into the cell in order to make the desired measurements.

In the second situation, the substrate of interest has to be small enough to be inserted into the sample slot in the electrochemical cell or the substrate of interest must have an edge of a limited size and orientation on which the cell can be fastened in order to make the desired electrochemical measurements.

FIG. 2 illustrates this latter type of prior art device. This figure corresponds to a commercially available electrochemical cell known as Princeton Applied Research Flat Cell Model K0235. Cell 70 comprises a glass cylinder 72 with ports 74 and 76 therein for receiving a counter electrode and a reference electrode (not shown). The cell is closed at one end by a plate 78 and at the other end by fixture 80. Fixture 80 has a slot 82 to permit a portion of sample 92 to be inserted therein. Screw 88 is threaded into wall 86 of fixture 80 to bias the sample 92 against wall 84 of fixture 80. Wall 84 of fixture 80 has an electrolyte opening 90 therein to permit electrolyte contained in cylinder 72 to contact the surface of sample 92. Plate 78 and fixture 80 are secured at each end of cylinder 72 by threaded rods 94 which are secured to plate 78 and fixture 80 by nuts 96.

In practice some sort of sealing means [not shown] would normally be provided around electrolyte opening 90 to seal opening 90 against the surface of sample 92. This might take the form of an O-ring, gasket or other suitable device. Electrolyte is then poured into the cylinder 72 to a suitable level and a reference electrode and a counter electrode are mounted in ports 74 and 76 and suspended in the electrolyte within cylinder 72. A known prior art potentiostat is connected to the working electrode [sample 92] and the reference and counter electrodes and any desired electrochemical measurements may be made.

Cell 70 is normally limited to handling samples of a limited size such that they can fit into the slot 82 in fixture 80 and such that they can be supported by cell 70. If it is desired to fasten cell 70 to a larger sample, the orientation and size of the portion of the sample which must enter slot 82 becomes extremely important. This portion has to be generally vertical and sized and oriented such that cell 70 can be fastened thereto. Since ports 74 and 76 are not normally sealed, cell 70 is clearly designed to function only in a generally horizontal orientation.

In certain instances it is known in the prior art to adhere a cylindrical electrochemical cell to a generally horizontal substrate of interest. The cell may comprise a section of non-metallic tubing which is open at the top and wherein the bottom end of the tubing is fastened to the substrate with adhesive. The substrate of interest thus becomes the bottom wall of the cell. There is no intent with this type of device that the cell be easily removable and repositionable. The adhesive used is quite strong and would require serious force to be applied for removal. The forces involved usually cause damage to the tubing and to the substrate.

Figure 3:
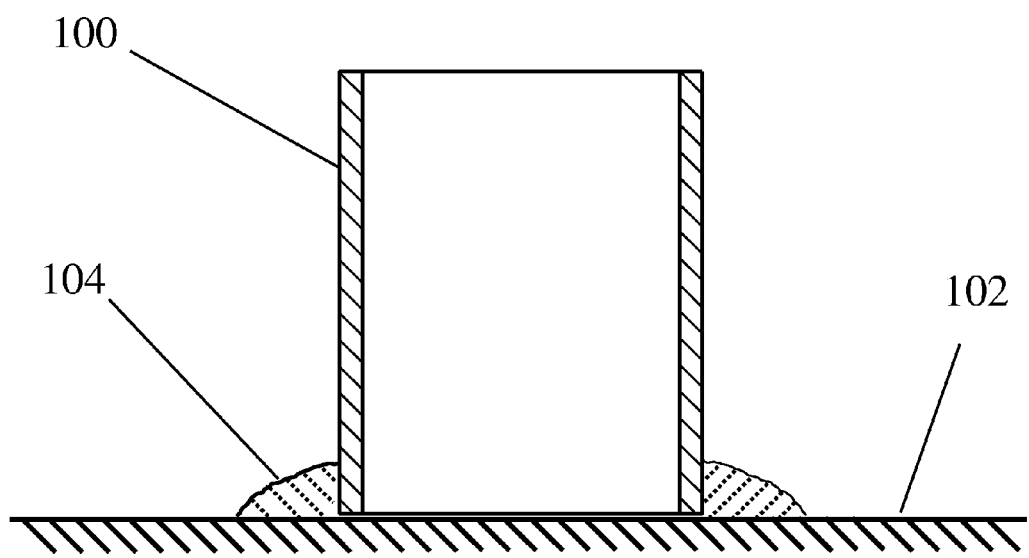
FIG. 3 shows a prior art electrochemical cell which can work with a substrate of indefinite size.

FIG. 3 illustrates this type of prior art device. Open cylinder 100 is adhered to substrate 102 by adhesive 104. Cylinder 100 may be made from any suitable non-metallic material, such as glass, PVC or other suitable plastic. Electrolyte is then poured into the cylinder 100 to a suitable level and a reference electrode [not shown] and a counter electrode [not shown] are suspended within the electrolyte. A known prior art potentiostat is connected to the working electrode [substrate 102] and the reference and counter electrodes and any desired electrochemical measurements may be made.

In contrast to the prior art devices, the electrochemical cell of the present invention even in its most basic form does not required damage to be done to the cell or to the substrate in order to take the desired electrochemical measurements. A minor cleaning of the surface in the area affected by the cell mounting means may be required. This would comprise removal of any contaminants or loose material which could adversely affect the mounting. Depending upon the type of electrochemical measurements being taken, any coating material in the immediate vicinity of the testing area might have to be removed to secure access to the underlying metal, but this may not be necessary if the cell is used to make electrochemical measurements on the coating of the substrate.

In addition, the mounting means of the present invention permits electrochemical measurements to be made on substrates of indefinite size, such as ships, planes, bridges or buildings. The surfaces to be measured do not have to be strictly planar and may, indeed, be somewhat curved.

Figure 4:
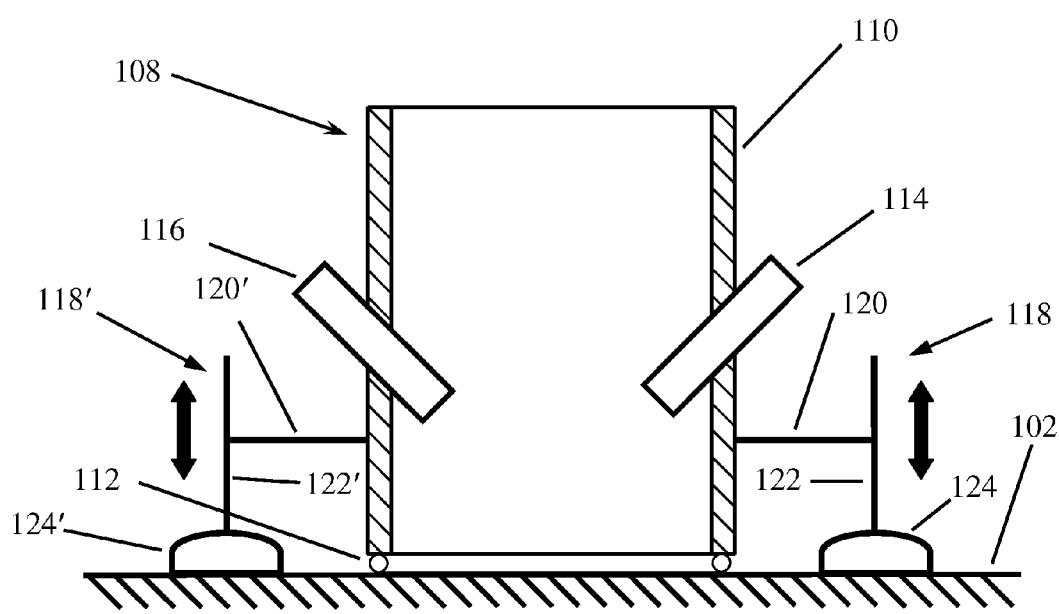
FIG. 4 shows the most basic electrochemical cell of the invention.

FIG. 4 shows an electrochemical cell 108 comprising a cylinder 110 which is open at the top end and has sealing means 112 attached to the bottom end. This may take the form of an O-ring, gasket or any other suitable sealing means. Ports 114 and 116 are provided for insertion of a reference electrode and a counter electrode (not shown). These ports are designed such that the port with an electrode inserted therein would be liquid tight. This could be accomplished, for example, by the use of a plug which held the electrode therein. The plug could be secured and sealed within port 114 and/or 116 using an O-ring, gasket, screw threads or any other suitable means.

At least one mounting means 118 is provided to removably and nondestructively secure call 108 to a surface of substrate 102. In this figure mounting means 118 and an identical mounting means 118' are shown. Mounting means 118, 118' provide for adjustment of the cell 108 towards and away from substrate 102. This allows for the bottom end of cylinder 110 to be biased against substrate 102 and permits sealing means 112 to seal cell 108 against substrate 102. Mounting means 118, 118' have a generally horizontal attachment arm 120, 120' which secures the mounting means to cylinder 110. In addition mounting means 118, 118' have a generally vertical leg 122, 122' to hold securing means 124, 124'. As shown, leg 122, 122' can move vertically on arm 120, 120'. Securing means 124, 124' may comprise a suction cup, a magnet, releasable adhesive means or any other device capable of releasably and nondestructively securing cell 108 to one surface of substrate 102. Certain applications may be such that only one mounting means 118 is necessary, however two mounting means 118 will be necessary in many applications and three mounting means 118 is considered the optimal number for general usage, although more may be provided as the situation requires. Each mounting means is independently adjustable in the vertical direction. This permits the cell 108 to be used on non-planar surfaces.

Operation:

In operation, substrate 102 would be cleaned as necessary for the desired measurements. This would involve cleaning in the area where securing means 124, 124' would contact substrate 102. In addition, the area of substrate which would be directly under the footprint of cylinder 110 would be cleaned and any coating in this area may have to be removed in order to make the desired electrochemical measurements. Cell 108 would be then be secured to substrate 102 using mounting means 118, 118'. The mounting means would be adjusted to bias cell 108 against the surface of substrate 102 to seal cell 108 to substrate 102 by compressing sealing means 112. A suitable reference electrode and suitable counter electrode would be secured in ports 114 and 116. The cell would be filled with a suitable electrolyte. A conventional prior art potentiostat (not shown) would be electrically connected to the reference electrode and the counter electrode. In addition, the potentiostat would be electrically connected to the working electrode (substrate 102) and the desired electrochemical measurements taken. When the necessary electrochemical measurements are completed, the cell is emptied of electrolyte and sealing means 124, 124' are removed from substrate 102. The potentiostat would be disconnected from the cell and the reference and counter electrodes removed and stored for further use. Any spilled electrolyte would be cleaned up and the substrate 102 would be returned to its original condition. This might involve mild cleaning in the area of securing means 124, 124' if a releasable adhesive is used in securing means 124, 124' or an even more minimal cleaning if securing means 124, 124' involve the use of suction cups or magnets. The surface of substrate 102 in the area of the bottom opening of cylinder 110 might have to be recoated if a coating was removed to make the desired measurements.

Figure 5:
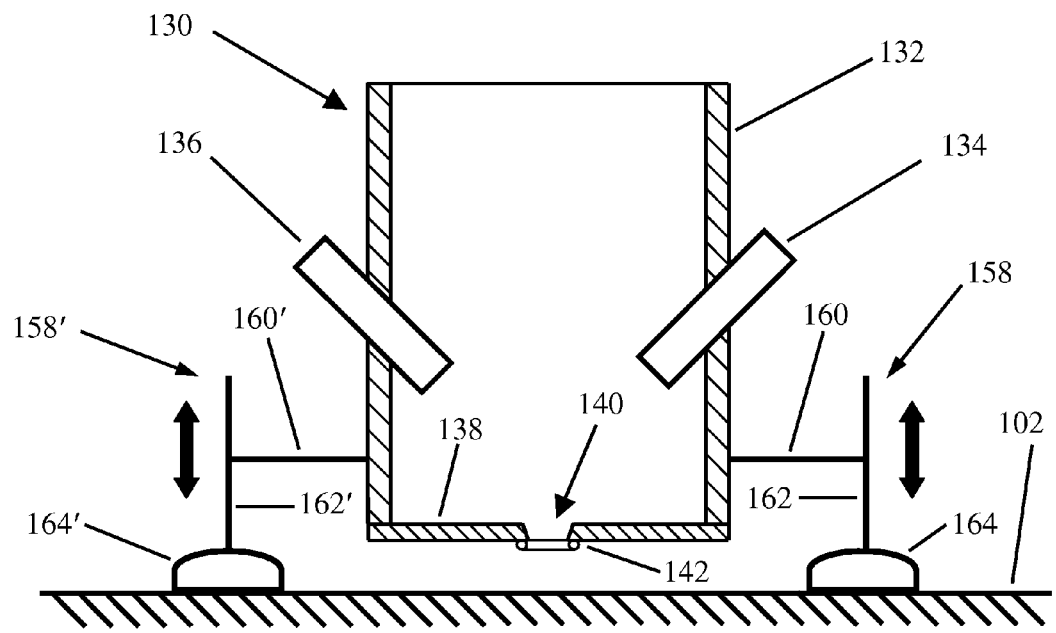
FIG. 5 shows a modification of the electrochemical cell shown in FIG. 4.

FIG. 5 shows a modification of the electrochemical cell of FIG. 4. The electrochemical cell 130 of FIG. 5 comprises a cylinder 132 which is open at the top end and has a plate 138 closing its bottom end. Plate 138 may be removably secured to the bottom of cylinder 132 or it may optionally be integral with cylinder 132. Plate 138 has an electrolyte opening 140 therein. This electrolyte opening 140 is provided with a sealing means 142 surrounding electrolyte opening 140 at the exterior surface of plate 138 to seal cylinder 132 and plate 138 to the surface of substrate 102. Sealing means 142 may take the form of an O-ring, gasket or any other suitable means. Ports 134 and 136 are provided for insertion of a reference electrode and a counter electrode (not shown). These ports are designed such that the port with an electrode inserted therein would be liquid tight. This could be accomplished, for example, by the use of a plug which held the electrode therein. The plug could be secured and sealed within port 134 and/or 136 using an O-ring, gasket, screw threads or any other suitable means.

At least one mounting means 158 is provided to removably and nondestructively secure call 108 to a surface of substrate 102. In this figure two mounting means 158, 158' are shown. Mounting means 158, 158' provide for adjustment of the cell 130 towards and away from substrate 102. This allows for the electrolyte opening 140 in plate 138 to be biased against substrate 102 and permits sealing means 142 to seal cell 130 against substrate 102.

Mounting means 158, 158' has a generally horizontal attachment arm 160, 160' which secures the mounting means to cylinder 132. In addition mounting means 158, 158' has a generally vertical leg 162, 162' to mount securing means 164, 164' to the mounting means. As shown, leg 162, 162' can move vertically on arm 160, 160'. Securing means 164, 164' may comprise a suction cup, a magnet, releasable adhesive means or any other device capable of releasably and nondestructively securing cell 108 to one surface of substrate 102.

Certain applications may be such that only one mounting means 158 is necessary, however two mounting means 158, 158' are considered necessary in most applications and three mounting means are considered the optimal number for general usage although more may be provided as desired. Each mounting means is independently adjustable in the vertical direction. This permits the cell 130 to be used on non-planar surfaces.

In operation, substrate 102 would be cleaned as necessary for the desired measurements. This would involve cleaning in the area where securing means 164, 164' would contact the surface of substrate 102. In addition, the area of substrate 102 which would be directly under the footprint of electrolyte opening 140 would be cleaned and any coating in this area may have to be removed in order to make the desired electrochemical measurements. Cell 130 would be then be secured to the surface of substrate 102 using mounting means 158, 158'. The mounting means would be adjusted to bias cell 130 against surface 102 to seal cell 130 to substrate 102 using sealing means 142. A suitable reference electrode and a suitable counter electrode (not shown) would be secured in ports 134 and 136. The cell would be filled with a suitable electrolyte. A conventional prior art potentiostat (not shown) would be electrically connected to the reference electrode and the counter electrode. In addition, the potentiostat would be electrically connected to the working electrode (substrate 102) and the desired electrochemical measurements taken.

When the desired electrochemical measurements have been collected, the electrolyte would be removed from cell 130, the potentiostat disconnected, and the reference and counter electrodes removed from ports 134 and 136. The cell 130 would then be removed from substrate 102 and any necessary cleaning of substrate 102 performed. Since the area of the electrolyte opening 140 is substantially less than the entire cross-section of cylinder 132, replacement of any coating of substrate 102 would be simpler than when using the electrochemical cell of FIG. 4.

Figure 6:
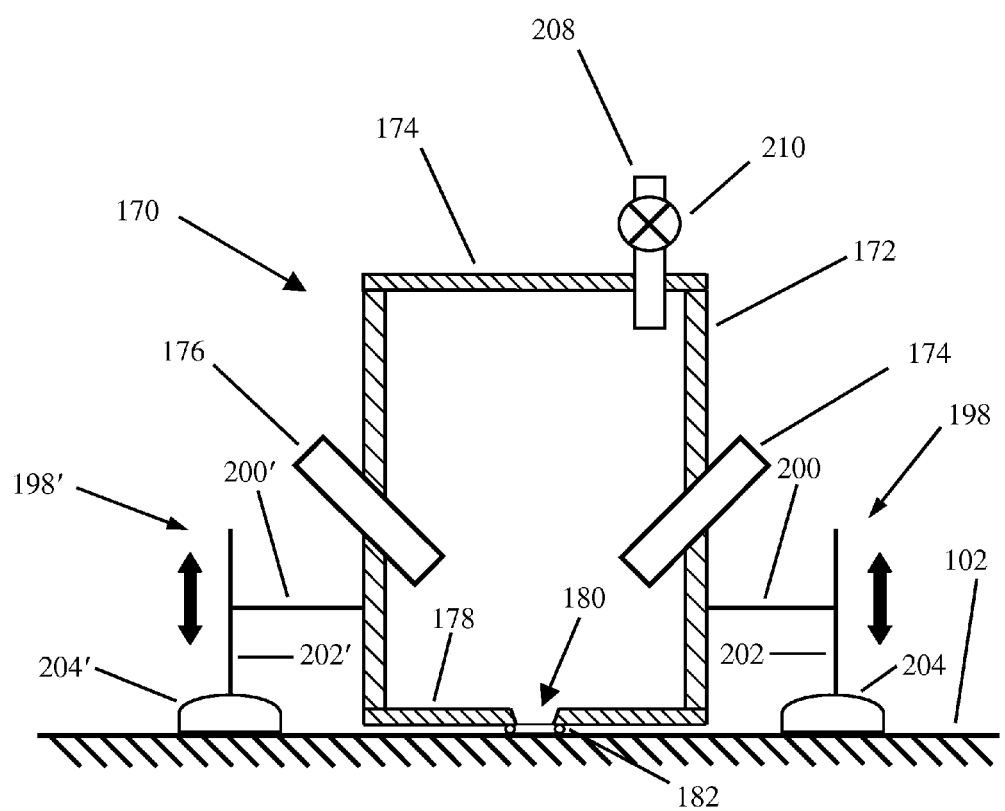
FIG. 6 shows a further modification of the electrochemical cell shown in FIG. 4.

FIG. 6 shows an electrochemical cell which is a further modification of the electrochemical cell shown in FIG. 4. The electrochemical cell 130 of FIG. 6 comprises a cylinder 172 which is closed at the top end by plate 174 and has a plate 178 closing its bottom end. Plates 174 and 178 may be removably secured to the cylinder 172 or they may optionally be integral with cylinder 172. Plate 178 has an electrolyte opening 180 therein. This electrolyte opening 180 is provided with a sealing means 182 surrounding electrolyte opening 180 at the exterior surface of plate 178 to seal cylinder 172 and plate 178 to the surface of substrate 102. Sealing means 182 may take the form of an O-ring, gasket or any other suitable means.

Ports 174 and 176 are provided for insertion of a reference electrode and a counter electrode (not shown). These ports are designed such that the port with an electrode inserted therein would be liquid tight. This could be accomplished, for example, by the use of a plug which held the electrode therein. The plug could be secured and sealed within port 174 and/or 176 using an O-ring, gasket, screw threads or any other suitable means.

Plate 174 has a filling/drain port 208 incorporated therein to permit the cell 170 to be filled with electrolyte. This filling/drain means incorporates a valve 210 to open and/or close port 208. This will permit the cell 170 to be conveniently emptied of electrolyte when the desired measurements have been taken as will be discussed below in the operation section.

At least one mounting means 198 is provided to removably and nondestructively secure cell 170 to a surface of substrate 102. In this figure two mounting means 198, 198' are shown. Mounting means 198, 198' provide for adjustment of the cell 170 towards and away from substrate 102. This allows for the electrolyte opening 180 in plate 178 to be biased against substrate 102 and permits sealing means 182 to seal cell 170 against substrate 102.

Mounting means 198, 198' have a generally horizontal attachment arm 200, 200' which secures the mounting means to cylinder 172. In addition mounting means 198, 198' has a generally vertical leg 202, 202' to mount securing means 204, 204' to the mounting means. As shown, leg 202, 202' can move vertically on arm 200, 200'. Securing means 204, 204' may comprise a suction cup, a magnet, releasable adhesive means or any other device capable of releasably and nondestructively securing cell 170 to one surface of substrate 102.

Certain applications may be such that only one mounting means 198 is necessary, however two mounting means 198, 198' are considered necessary in most applications and three mounting means are considered the optimal number for general usage although more may be provided as desired. Each mounting means is independently adjustable in the vertical direction. This permits the cell 170 to be used on non-planar surfaces.

Operation:

In operation, substrate 102 would be cleaned as necessary for the desired measurements. This would involve cleaning in the area where securing means 204, 204' would contact the surface of substrate 102. In addition, the area of substrate 102 which would be directly under the footprint of electrolyte opening 180 would be cleaned and any coating in this area may have to be removed in order to make the desired electrochemical measurements. Cell 170 would be then be secured to the surface of substrate 102 using mounting means 198, 198'. The mounting means would be adjusted to bias cell 170 against surface 102 to seal cell 170 to substrate 102 using sealing means 182. A suitable reference electrode and a suitable counter electrode (not shown) would be secured in ports 174 and 176. The cell would be filled with a suitable electrolyte using filling/draining port 208. A conventional prior art potentiostat (not shown) would be electrically connected to the reference electrode and the counter electrode. In addition, the potentiostat would be electrically connected to the working electrode (substrate 102) and the desired electrochemical measurements taken.

When the desired electrochemical measurements have been collected, the electrolyte can be removed from cell 170 by closing valve means 210 and then quickly removing cell 170 from substrate 102 and then inverting the cell 170. A small amount of electrolyte would be spilled during this procedure, but most all of the electrolyte will be secured inside cell 170. Then valve means 210 may be used to drain the used electrolyte where and when desired. The potentiostat (not shown) can be disconnected, and the reference and counter electrodes removed from ports 174 and 176. At this time any necessary cleaning of substrate 102 performed. Since the area of the electrolyte opening 180 is substantially less than the entire cross-section of cylinder 172, replacement of any coating of substrate 102 would be simpler than when using the electrochemical cell of FIG. 4.

Figure 7:
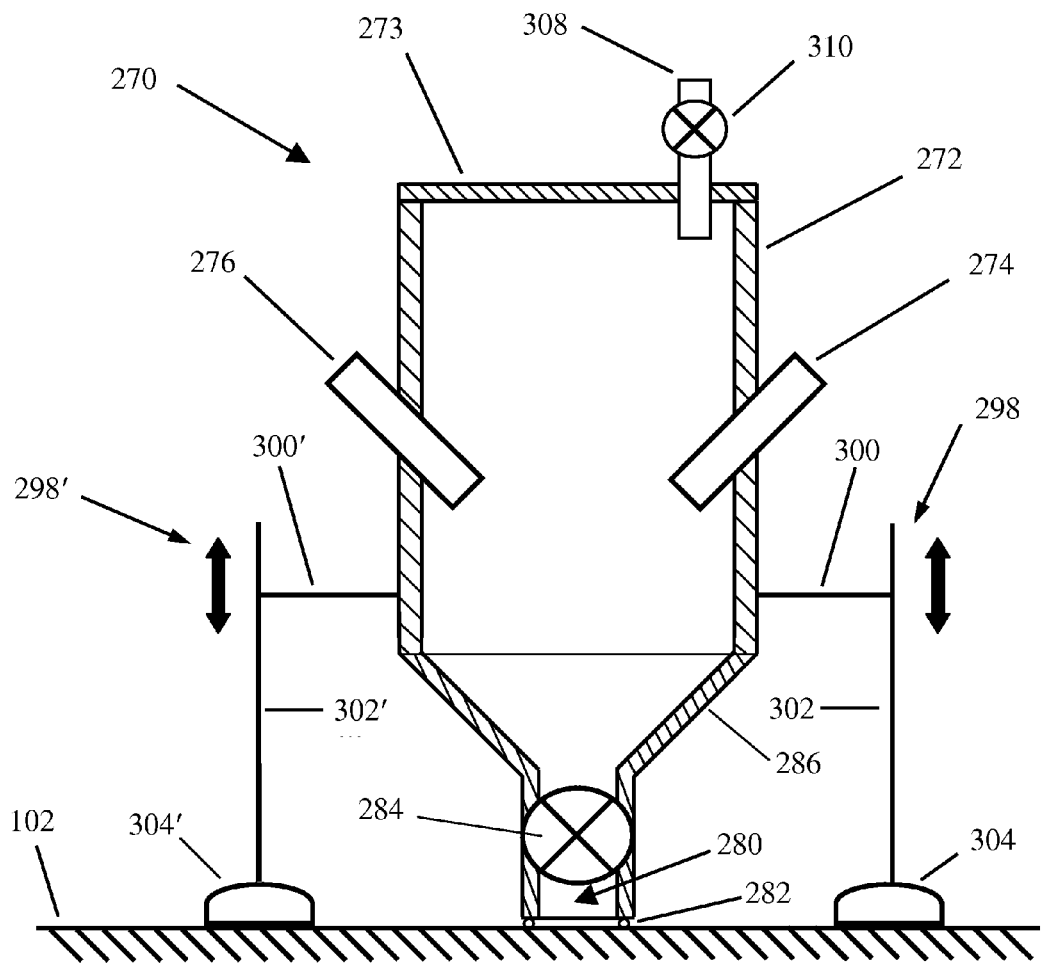
FIG. 7 shows a further modification of the electrochemical cell shown in FIG. 4.

FIG. 7 shows a further modification of the electrochemical cell shown in FIG. 4. The electrochemical cell 270 of FIG. 7 comprises a cylinder 272 which is closed at the top end by plate 273 and has a necked-down portion 286 closing its bottom end. Plates 273 and necked-down portion 286 may be removably secured to the cylinder 272 or they may optionally be integral with cylinder 272. Necked-down portion 286 has an electrolyte opening 280 therein. This electrolyte opening 280 is provided with a sealing means 282 surrounding electrolyte opening 280 at the exterior surface of necked-down portion 286 to seal cell 270 to the surface of substrate 102. Sealing means 282 may take the form of an O-ring, gasket or any other suitable means.

Ports 274 and 276 are provided for insertion of a reference electrode (not shown) and a counter electrode (not shown). These ports are designed such that the port with an electrode inserted therein would be liquid tight. This could be accomplished, for example, by the use of a plug which held the electrode therein. The plug could be secured and sealed within port 274 and/or 276 using an O-ring, gasket, screw threads or any other suitable means.

Plate 273 has a filling/drain port 308 incorporated therein to permit the cell 270 to be filled with electrolyte. This filling/drain means incorporates a valve 310 to open and/or close port 308. This will permit the cell 270 to be conveniently emptied of electrolyte when the desired measurements have been taken as will be discussed below in the operation section.

Necked-down portion 286 is provided with a valve 284 near electrolyte opening 280. This permits the electrolyte opening 280 to be opened or closed. Valve 284 may be a rotary valve, a slide valve or any other suitable type of valve.

At least one mounting means 298 is provided to removably and nondestructively secure cell 270 to a surface of substrate 102. In this figure two mounting means 298, 298' are shown. Mounting means 298, 298' provide for adjustment of the cell 270 towards and away from substrate 102. This allows for the electrolyte opening 280 in necked-down portion 286 to be biased against substrate 102 and permits sealing means 282 to seal cell 270 against substrate 102.

Mounting means 298 and 298' have a generally horizontal attachment arm 300, 300' which secures the mounting means to cylinder 272. In addition mounting means 298, 298' has a generally vertical leg 302, 302' to mount securing means 304, 304' to the mounting means. As shown, legs 302 and 302' can move vertically on arms 300, 300'. Securing means 304, 304' may comprise a suction cup, a magnet, releasable adhesive means or any other device capable of releasably and nondestructively securing cell 270 to one surface of substrate 102.

Certain applications may be such that only one mounting means 298 is necessary, however two mounting means 298, 298' are considered necessary in most applications and three mounting means are considered the optimal number for general usage although more may be provided if desired or necessary. Each mounting means is independently adjustable in the vertical direction. This permits the cell 270 to be used on non-planar surfaces.

Operation:

In operation, substrate 102 would be cleaned as necessary for the desired measurements. This would involve cleaning in the area where securing means 304, 304' would contact the surface of substrate 102. In addition, the area of substrate 102 which would be directly under the footprint of electrolyte opening 280 would be cleaned and any coating in this area may have to be removed in order to make the desired electrochemical measurements. Cell 270 would be then be secured to the surface of substrate 102 using mounting means 298, 298'. The mounting means would be adjusted to bias cell 270 against surface 102 to seal cell 270 to substrate 102 using sealing means 282. A suitable reference electrode (not shown) and a suitable counter electrode (not shown)

would be secured in ports 274 and 276. The cell would be filled with a suitable electrolyte using filling/draining port 308. During the filling process, valve 284 would be closed. A conventional prior art potentiostat (not shown) would be electrically connected to the reference electrode and the counter electrode. In addition, the potentiostat would be electrically connected to the working electrode (substrate 102). At this time valve 284 would be opened to permit electrolyte from the interior of the cell 270 to access the working electrode (substrate 102). The desired electrochemical measurements may then be taken.

When the desired electrochemical measurements have been collected, the cell 270 may be removed from substrate 102 after closing valve means 310 and 284. Securing means 304, 304' would be removed from substrate 102 and the cell 270 lifted off substrate 102. A small amount of electrolyte might be spilled on the surface of substrate 102 in the removal process, but most all of the electrolyte will be secured inside cell 270. The small amount spilled can be easily cleaned up. Once cell 270 is separated from substrate 102 and the potentiostat leads are disconnected, electrolyte may be drained from cell 270 using valves 284 and/or 310. Then the reference and counter electrodes (not shown) may be removed from ports 274 and 276.

At this time any necessary cleaning of substrate 102 performed. Since the area of the electrolyte opening 280 is substantially less than the entire cross-section of cylinder 272 and since valves 284 and 310 operate to secure most all of the electrolyte inside cell 270 during removal, clean-up of spilled electrolyte is minimal. At this time, any necessary cleanup of the areas of substrate 102 under securing means 304, 304' can be performed and any coating of substrate 102 removed because of the electrochemical measurement process can be replaced in order to restore substrate 102 to its original condition.

Figure 8:
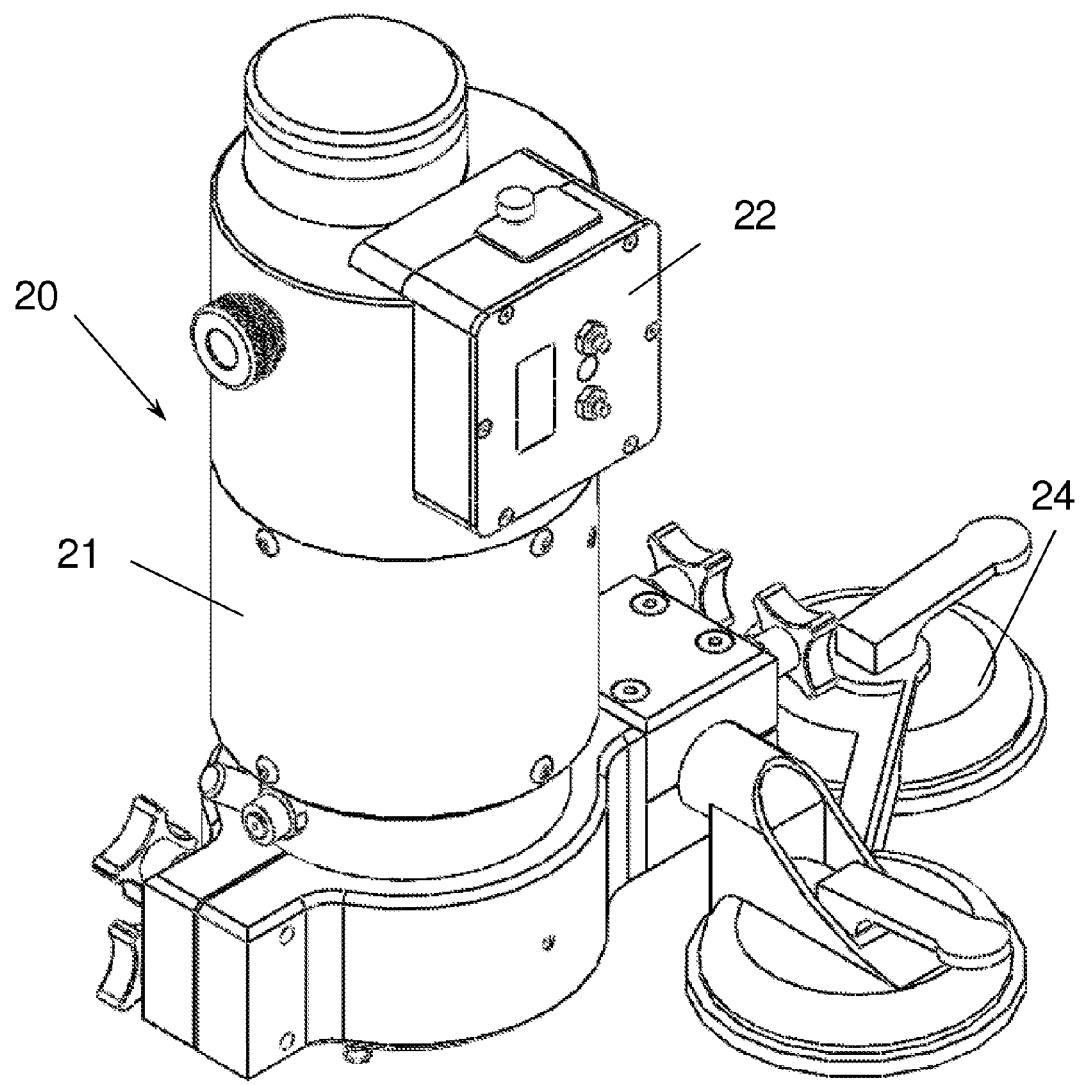
FIG. 8 shows an-isometric view of the probe of the second embodiment of the invention.

FIG. 8 shows an isometric view of the probe 20 of the second embodiment of the invention. The probe housing 21 is shown with the electronics component housing 22 and the attachment mechanism 24. In this drawing the attachment mechanism comprises suction cups, but it could also be magnets, clamps, screws, bolts, or other means of attachment.

Figure 9:
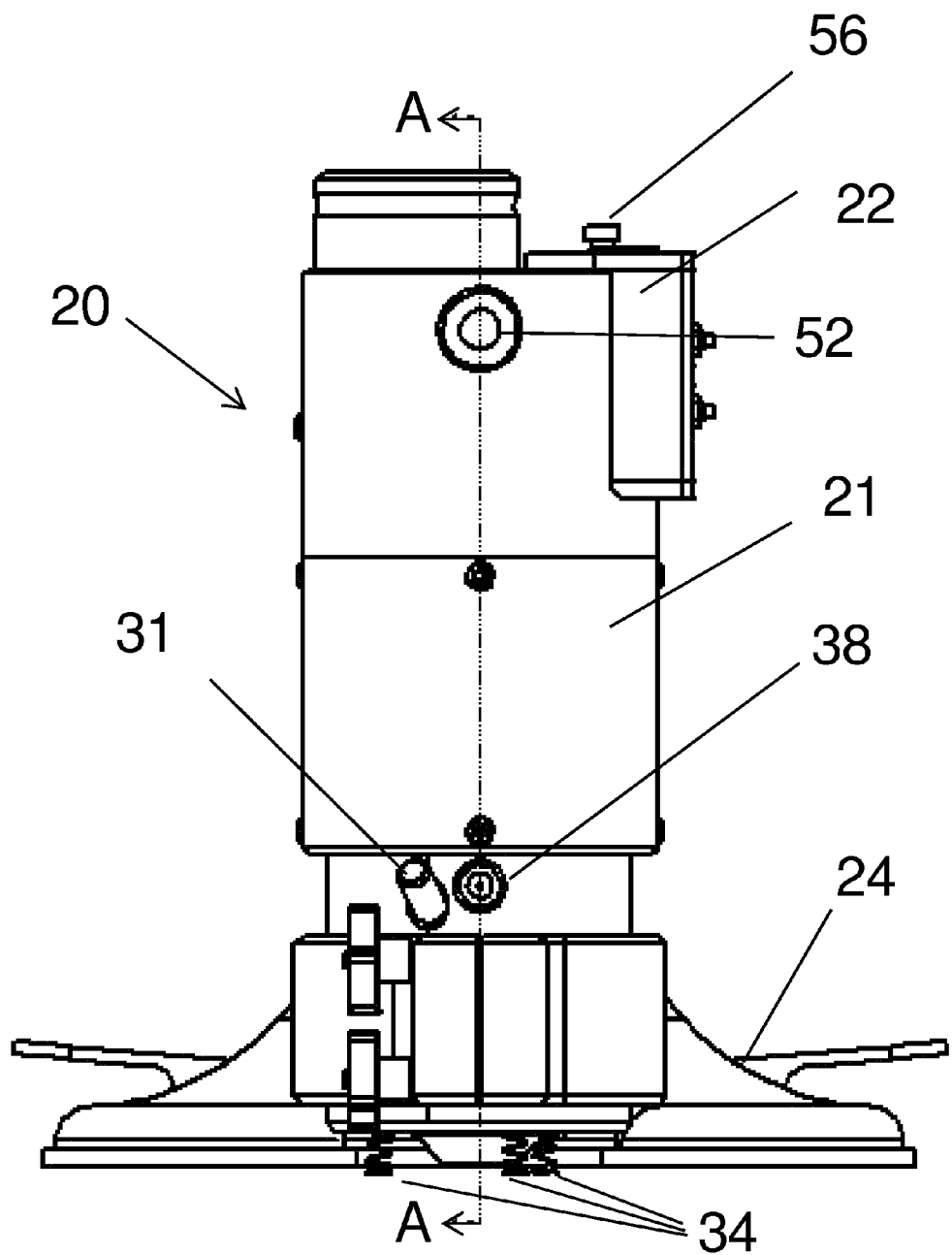
FIG. 9 shows a side view of the probe.

FIG. 9 shows another view of the probe 20. Electrical contact to a bare (uncoated) surface substrate is provided by springs 34. These springs provide a means to apply a voltage or current to a substrate of interest. The springs also provide a means for making electrical measurements. For a coated substrate, electrical connection would be provided by a separate lead (not shown). The port 31 allows the reference electrode 32 in FIG. 10 to be inserted into the probe and easily replaced from the outside of the probe. An air/liquid separator 38 allows the air to escape from the measurement chamber as it is being flooded. The thumb screw 52 holds in place an optional removable container filled with electrolyte.

The electronics component 50 (FIGS. 12 and 14) is contained in housing 22. The interface connector 56 allows for connection to a computer or other device to enable programming the electronics component 50 and to output data. In addition, the probe could be powered with electrical energy supplied via connector 56. The data transfer and programming can be accomplished via connector 56 or by other means such as a wireless transmission.

Figure 10:
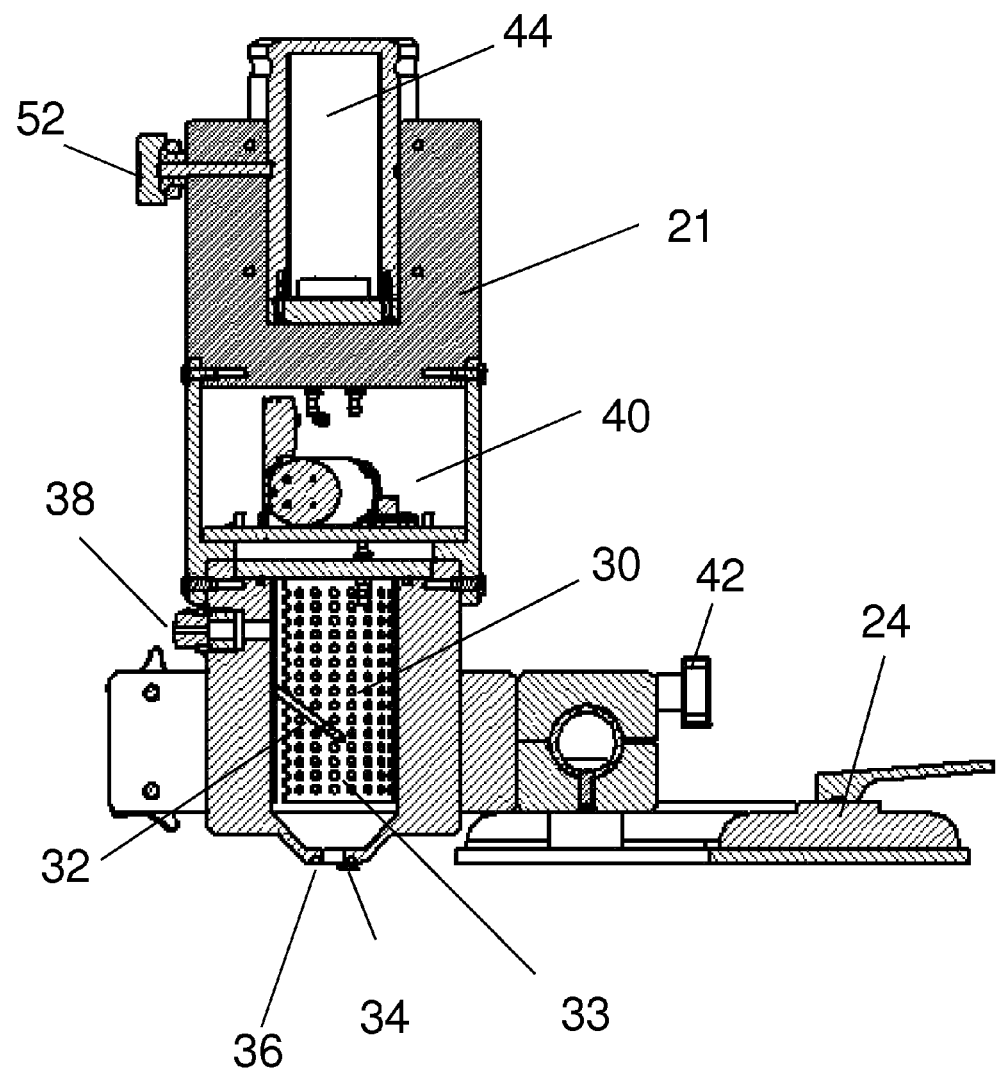
FIG. 10 shows a cross-sectional view along A-A of FIG. 9.

FIG. 10 shows a cross-sectional view of the probe along line A-A of FIG. 9. It shows the probe housing 21 with the attachment mechanism 24. The analytical chamber 30 is sealed to the substrate surface (not shown) by an o-ring 36. Electrical contact to a bare (uncoated) surface is provided by springs 34. For a coated substrate, electrical connection is would be provided by a separate lead (not shown). The reference electrode 32 and the counter electrode 33 are mounted in analytical chamber 30. The electrolyte reservoir 44 holds the electrolyte until it is transferred to the analytical chamber 30 with the pumps and valves in the fluidics compartment 40. The electrolyte reservoir 44 may be a refillable tank (not shown) which is integral with probe housing 21 or, more preferably, a removable container filled with electrolyte which can be held in place by thumb screw 52.

Figure 12:
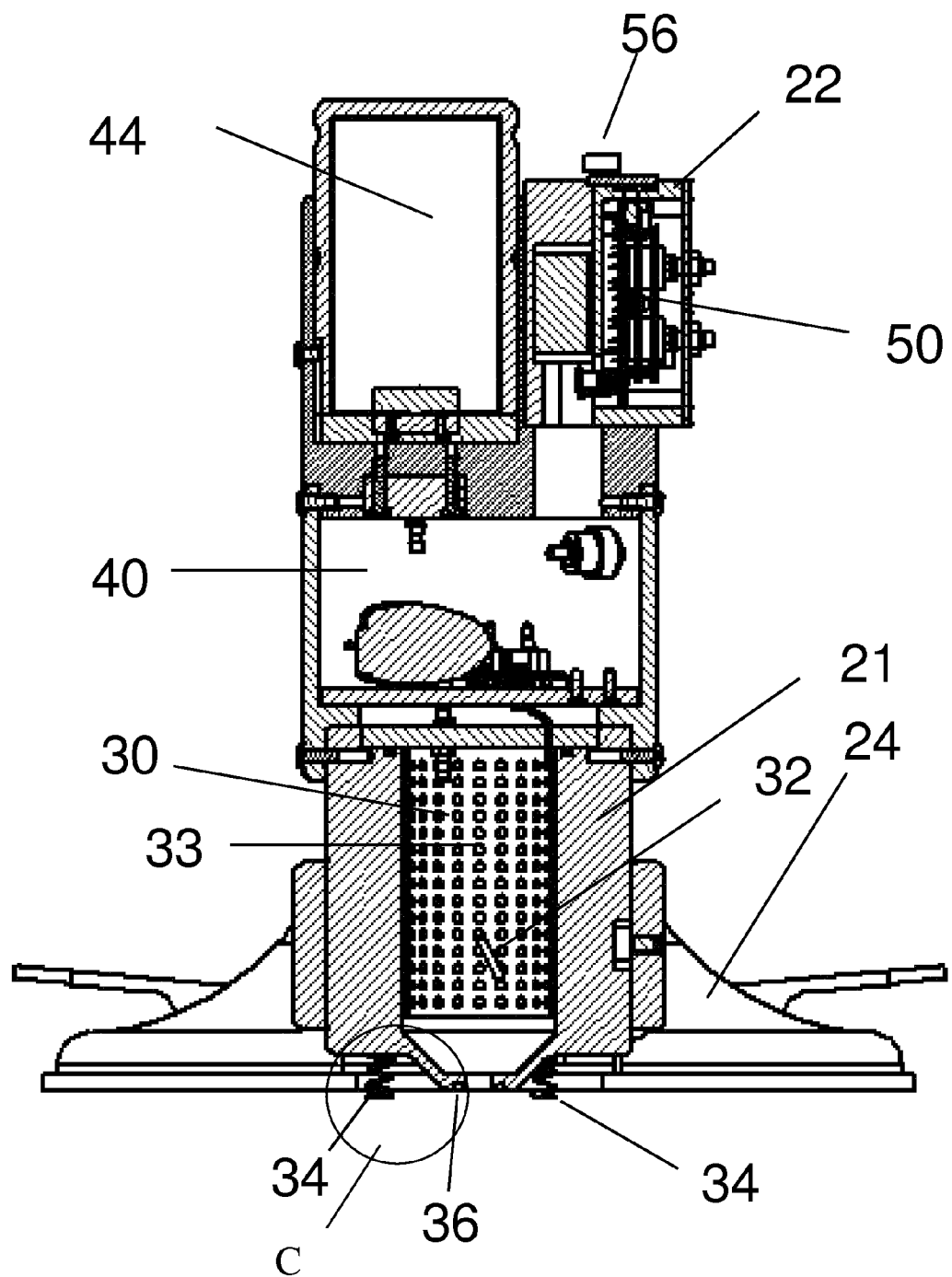
FIG. 12 shows a cross-sectional view along B-B of FIG. 11.

Reference electrode 32 could be any of several commercially available reference electrodes such as a saturated calomel electrode (SCE) or any other electrode suitable for the type of electrochemical measurement desired. In FIGS. 10 and 12, reference electrode 32 is illustrated as a rod-type electrode. The counter electrode 33 is illustrated in FIGS. 3b and 4b as a stainless steel mesh but it could take other forms such as a stainless steel or graphite rod or any other type of electrode suitable for the measurement desired. The choice of a suitable electrolyte would depend upon the exact type of measurement or test being performed. For example, in naval or marine corrosion tests, the electrolyte might be a saline solution to simulate sea water. Alternatively the electrolyte might be an acidic solution, an alkaline solution or a neutral solution depending upon the type of test being performed.

Figure 11:
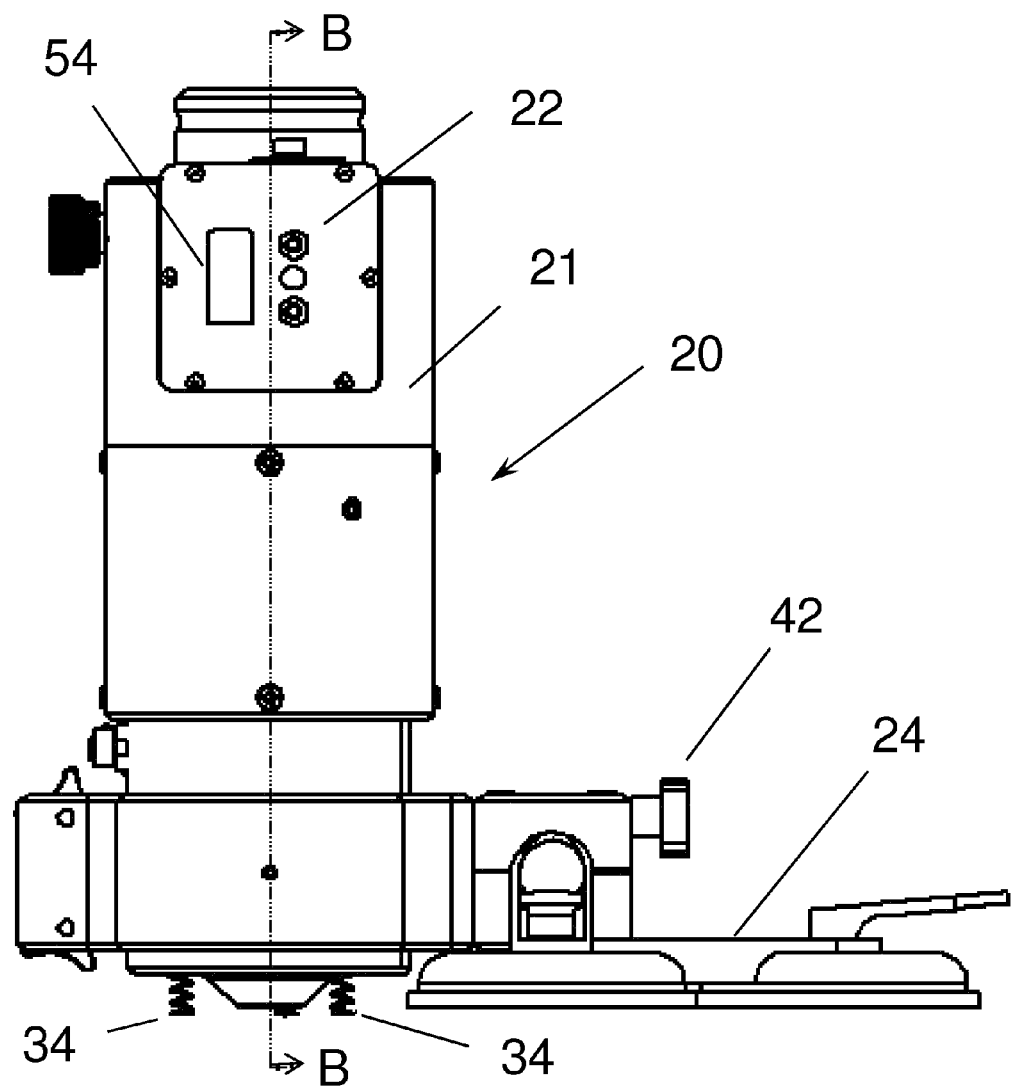
FIG. 11 shows another side view of the probe.

FIG. 11 shows a second view of the probe 20 showing the probe housing 21 with the attachment mechanism 24. Control 42 allows adjustment of the probe height to assure sealing to the substrate. Electrical contact to a bare (uncoated) substrate is provided by springs 34. For a coated substrate, electrical connection would be provided by a separate lead (not shown). Digital display 54 is mounted in electronics component housing 22.

FIG. 12 shows a cross-sectional view of the probe along line B-B of FIG. 11 showing the probe housing 21 with the attachment mechanism 24. The electrolyte reservoir 44 holds the electrolyte until it is transferred to the analytical chamber 30 with the pumps and valves in the fluidics compartment 40.

Figure 13:
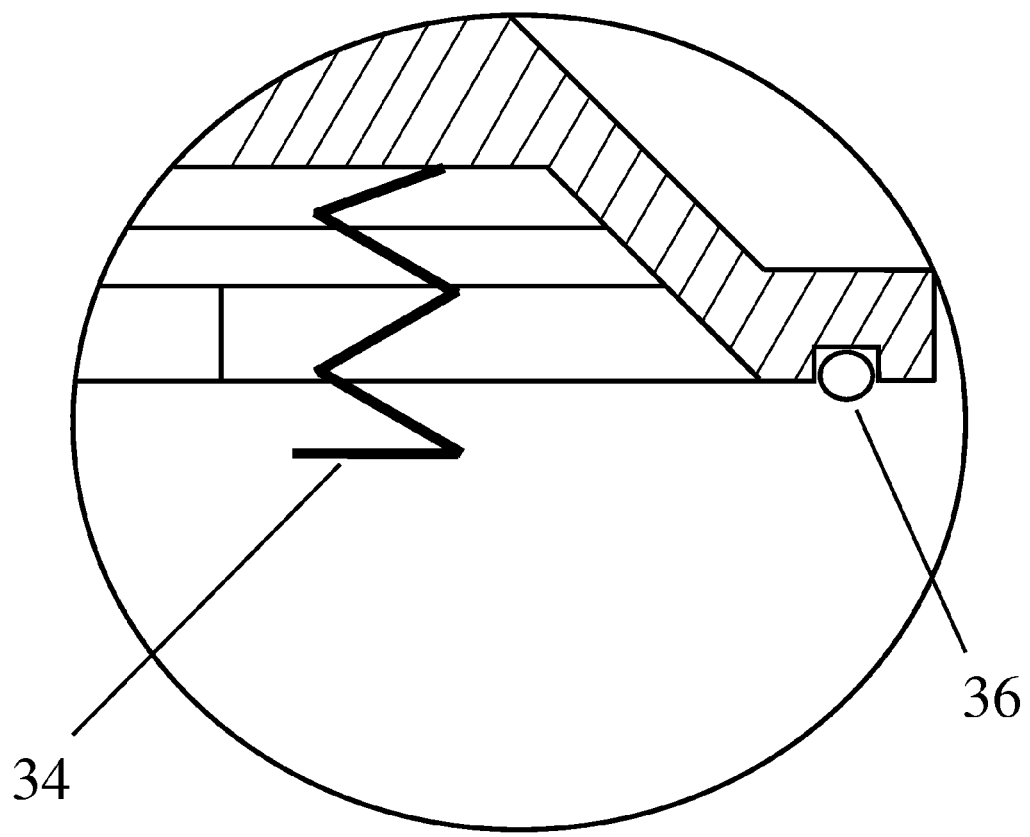
FIG. 13 shows a closer view of area C of FIG. 12.

FIG. 13 shows a detail of area C of FIG. 12 showing one spring 34 and o-ring 36.

Figure 14:
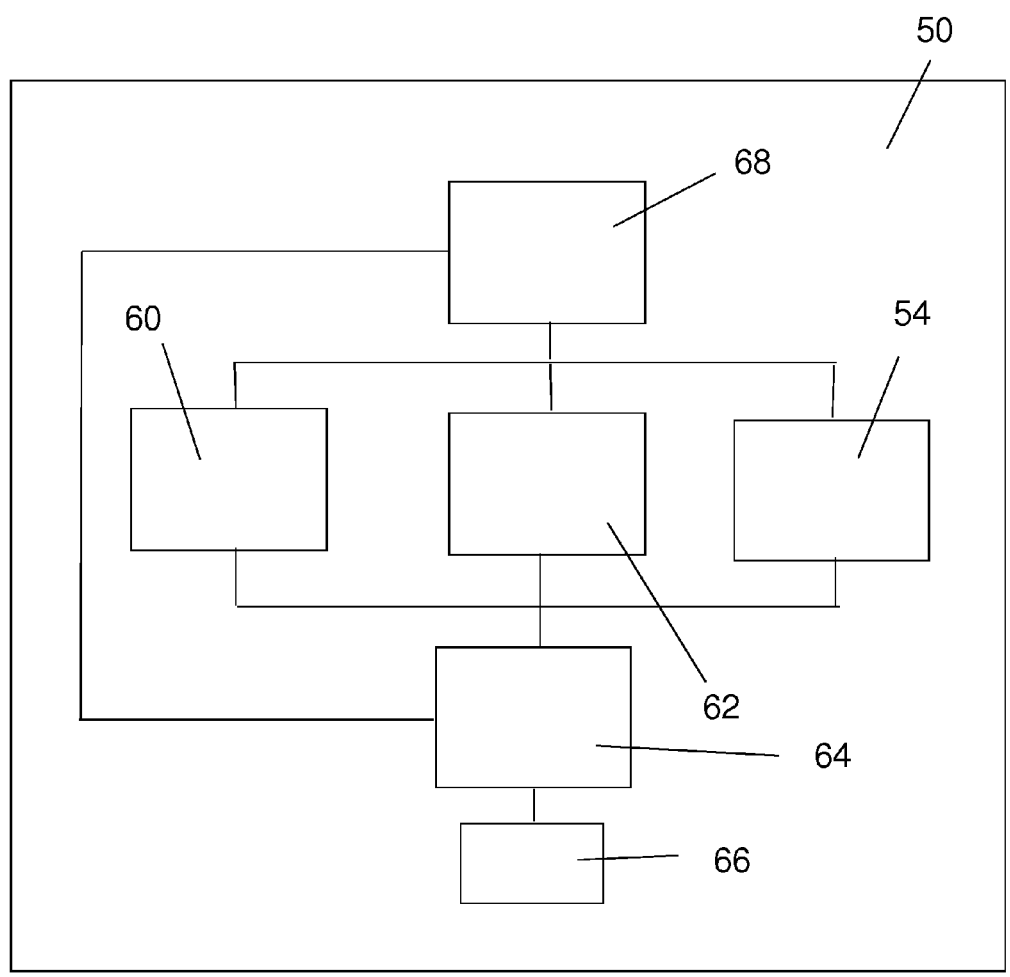
FIG. 14 shows a block diagram of the electronics component.

FIG. 14 shows a block diagram of the electronics component 50 comprising potentiostat 60, fluidics control 62, digital display 54, and input/output means 66 all controlled by microprocessor 64. Input/output means 66 enables programming instruction input and data output to an external computer or other device (not shown). An optional power supply 68 may be part of electronics component 50 or power may be supplied from a source external to the probe 20. Input/output means 66 may also provide for wireless transfer of information.

Potentiostat 60 can apply a potential between reference electrode 32 and a surface of a substrate. It can also apply a current between counter electrode 33 and a surface of a substrate. Potentiostat 60 also has an electrometer capable of measuring the potential between a surface of a substrate and reference electrode 32 as a function of time or as a function of applied current and also capable of measuring a current between counter electrode 33 and a surface of a substrate as a function of time or as a function of applied voltage. The applied potential and/or current may be constant, they may vary (e.g. be ramped). The applied potential and/or current may be either AC or DC. When the applied potential and/or current are AC, the frequency may be varied.

Microprocessor 64 preferably includes a clock to provide time stamp information and storage means to store the collected data.

Figure 15:
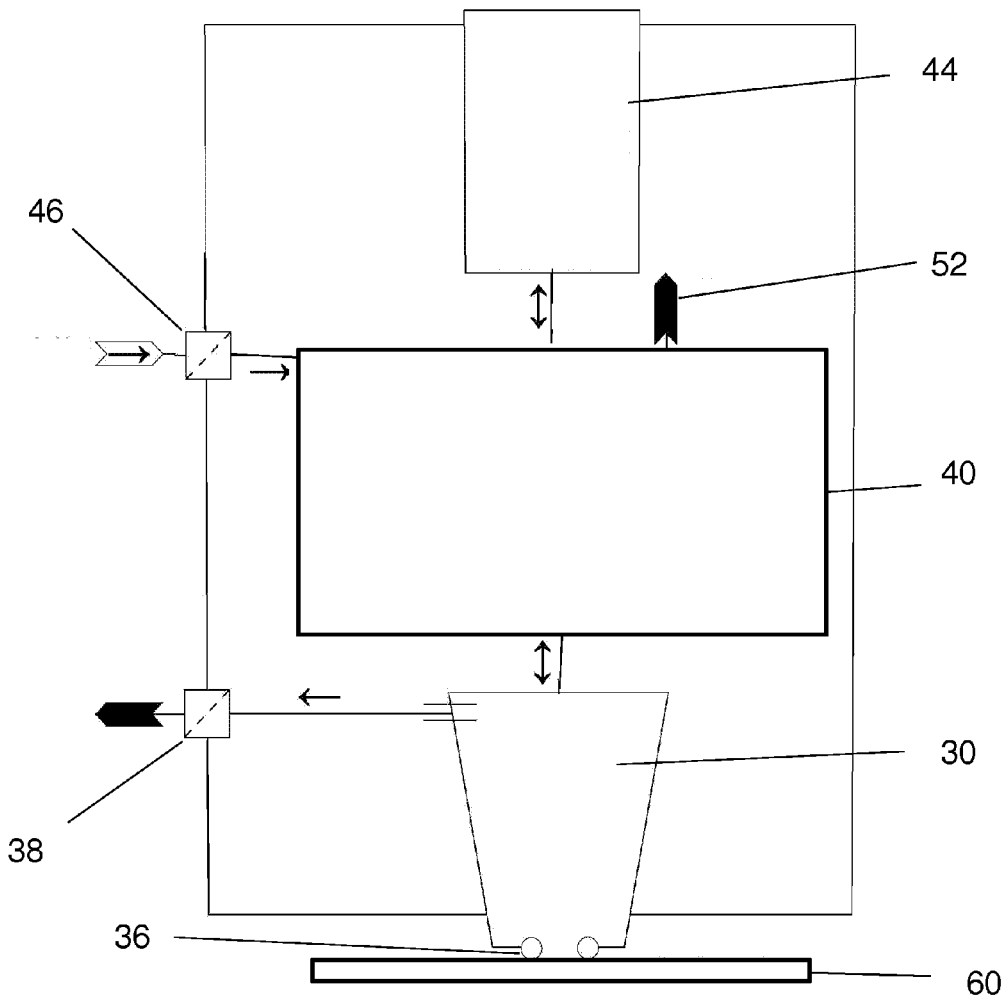
FIG. 15 shows a block diagram of the fluidics component.

FIG. 15 shows a block diagram of the fluidics system including the reservoir tank 44, the pumps and valves system 40, the analytical chamber 30 sealed with o-ring 36 to the material of interest 60. Also shown is the air separator and valve 38 to allow the air in the analytical chamber 30 to be exhausted during the filling operation. The air filter 46 allows air to be readmitted to the analytical chamber 30 during the draining operation. Emergency vent 52 allows air to enter or leave the analytical chamber in case of an under or over pressure event.

Operation:

An operator or inspector will prepare the surface to be examined in a manner suitable for the measurement to be made. This preparation could include a simple cleaning of the surface, light abrasion to expose a fresh surface, heavy abrasion or grit blasting to remove material such as a paint coating if the underlying metal is to be examined. The operator would mount the apparatus onto the surface using suction cups, magnets, or other attachment means. The operator would then program the unit to take whatever electrochemical measurements are desired. These measurements could include a potential sweep or hold with the current being measured as a function of potential or of time, a current sweep or hold with the voltage being measured as a function of current or time, an oscillatory (ac) potential with the frequency being swept or held with the current being measured as a function of frequency, or the open circuit potential and current being measured as a function of time. The electrolyte would be transferred from the reservoir to the analysis chamber and the measurements being acquired either immediately or after an appropriate hold time. After the measurements are completed, the electrolyte would be transferred back to the reservoir and the unit removed from the structure. Data could then be transferred to a portable computer or similar device for analysis.

Figure 16:
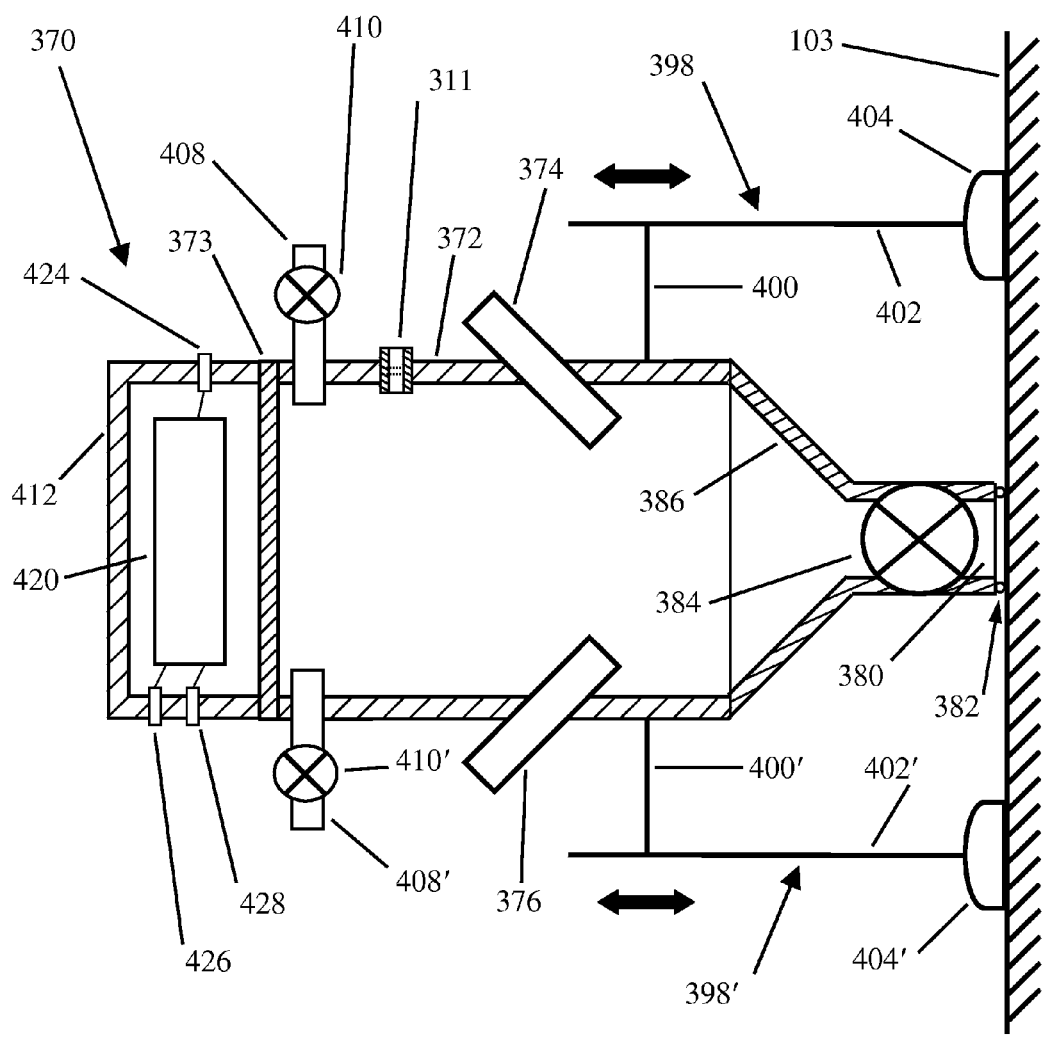
FIG. 16 shows the third embodiment of the invention mounted to a vertical substrate.

FIG. 16 shows the third embodiment of the electrochemical cell of the invention mounted to a generally vertical surface 103. The previous electrochemical cells have all been illustrated as taking electrochemical measurements on horizontal substrates. The electrochemical cell of this invention may be used to make electrochemical measurements on substrates which are not horizontal. In particular the closed cell embodiments as shown in FIGS. 6 and 7 are suitable for making measurements on vertical substrates. Since the mounting means will mount the cell to essentially any substrate, measurements can even be made on substrates which are inclined past vertical. In addition, the previous embodiments were designed for use with a conventional prior art potentiostat. It is possible to provide an electronics package to the previous embodiments and give them the capability to function without an external potentiostat. The embodiment shown in FIG. 16 is particularly suited for making such measurements.

The electrochemical cell 370 of FIG. 16 comprises a cylinder 372 which is closed at one end by plate 373 and has a necked-down portion 386 closing the other end. Plate 373 and necked-down portion 386 may be removably secured to the cylinder 372 or they may optionally be integral with cylinder 372. Necked-down portion 386 has an electrolyte opening 380 therein. This electrolyte opening 380 is provided with a sealing means 382 surrounding electrolyte opening 380 at the exterior surface of necked-down portion 386 to seal cell 370 to the surface of a substrate 103. Sealing means 382 may take the form of an O-ring, gasket, releasable adhesive or any other suitable means.

Ports 374 and 376 are provided for insertion of a reference electrode (not shown) and a counter electrode (not shown). These ports are designed such that the port with an electrode inserted therein would be liquid tight. This could be accomplished, for example, by the use of a plug which held the electrode therein. The plug could be secured and sealed within port 374 and/or 376 using an O-ring, gasket, screw threads, releasable adhesive or any other suitable means.

A filling/drain port 408 is incorporated into a suitable portion of cylinder 372 in order to permit the cell 370 to be filled with electrolyte when cylinder 372 is disposed in a generally horizontal position as it would be if cell 370 was secured to a generally vertical substrate 103. This filling/drain means incorporates a valve 410 to open and/or close port 408. A similar filling/drain port 408' is provided at a suitable location on cylinder 372 generally opposite to filling/drain port 408. Filling/drain port 408' has a valve 410' which permits filling/drain port 408' to be opened or closed. This provision of a filling/drain port 408' will permit the cell 370 to be conveniently emptied of electrolyte while cell 370 remains mounted to the generally vertical substrate 103. This will be further discussed below in the operation section.

An air-liquid separator 311 is provided in a portion of cylinder 372 near port 408. This permits gasses (e.g. air) trapped inside cell 370 to escape while the cell 370 is being filled with electrolyte. Air-liquid separator 311 does not have to be near the port 408. Other locations could be used as desired. The air-liquid separator simply has to be in suitable position so as to permit gasses to be exhausted from cell 370 as electrolyte is introduced therein. It is assumed, herein, that cell 370 would usually be mounted to the generally vertical substrate prior to filling the cell with electrolyte although this is not absolutely necessary.

Necked-down portion 386 is provided with a valve 384 near electrolyte opening 380. This permits the electrolyte opening 380 to be opened or closed. Valve 384 may be a rotary valve, a slide valve or any other suitable type of valve.

Housing 412 is secured to plate 373. This housing contains electronics component 420 which comprises a miniature potentiostat and the necessary means to initiate, monitor and control the electrochemical measurement process. Electronic component 420 also has means therein to store the electrochemical measurements when they are taken and means to output said stored measurements when desired. This electronics component is similar to electronics component 50 shown in FIGS. 12 and 14 and described earlier. Jack 424 is provided in housing 412 to permit an electrical connection from the electronics component 420 to a counter electrode (not shown). Jack 426 is provided in housing 412 to enable electrical connection between the electronic component 420 and the working electrode (in this instance, generally vertical substrate 103). Jack 428 is provided to enable electrical connection between electronics component 420 and a reference electrode (not shown).

At least one mounting means 398 is provided to removably and nondestructively secure cell 370 to a surface of generally vertical substrate 103. In this figure two such mounting means 398, 398' are shown. Mounting means 398, 398' provide for adjustment of the cell 370 towards and away from generally vertical substrate 103. This allows for the electrolyte opening 380 in necked-down portion 386 to be biased against substrate 103 and permits sealing means 382 to seal cell 370 against substrate 103.

Mounting means 398 and 398' have an attachment arm 400, 400' which secures the mounting means to cylinder 372. In addition mounting means 398, 398' have a leg 402, 402' to mount securing means 404, 404' to the mounting means. As shown, legs 402 and 402' can move along the longitudinal axis of cylinder 372 across arms 400, 400'. Securing means 404, 404' may comprise suction cups, magnets, releasable adhesive means or any other device capable of releasably and nondestructively securing cell 370 to one surface of generally vertical substrate 103.

It is possible that two mounting means 398, 398' would be sufficient to mount cell 370 to generally vertical substrate 103 but it is more likely that three such mounting means would be considered the optimal number for a vertical measurement. Obviously, more than three mounting means could be used, if desired. Each mounting means is independently adjustable along the longitudinal axis of cylinder 372 in order to permit the cell 370 to be used on non-planar surfaces.

Operation:

In operation, substrate 103 would be cleaned as necessary for the desired measurements. This would involve cleaning in the area where securing means 404, 404' would contact the surface of substrate 103. In addition, the area of substrate 103 which would be directly under the footprint of electrolyte opening 380 would be cleaned and any coating in this area may have to be removed in order to make the desired electrochemical measurements.

Cell 370 would then be secured to the surface of generally vertical substrate 103 using mounting means 398, 398'. The mounting means would be adjusted along the longitudinal axis of cylinder 372 to bias cell 370 against surface 103 in order to seal cell 370 to substrate 103 using sealing means 382. A suitable reference electrode (not shown) and a suitable counter electrode (not shown) would be secured in ports 374 and 376.

Electrical connections between electronics component 420 and the reference and counter electrodes would be made using jacks 428 and 424. In addition, electronics component 420 would be electrically connected to the working electrode (generally vertical substrate 103) using jack 426. The cell would be filled with a suitable electrolyte using filling/draining port 408. During the filling process, valves 384 and 410' would be closed. When the cylinder 372 is filled with electrolyte, valve 384 would be opened to permit electrolyte from the interior of the cell 370 to access the working electrode (generally vertical substrate 103). The desired electrochemical measurements may then be taken.

When the measurements have been collected, the cell 370 may be removed from generally vertical substrate 103 after making sure that valve means 410, 410' and 384 are closed. Securing means 404, 404' would be removed from generally vertical substrate 103 and the cell 370 lifted off. A small amount of electrolyte might be spilled in the removal process, but most all of the electrolyte will be secured inside cell 370. The small amount spilled can be easily be cleaned up. Once cell 370 is separated from generally vertical substrate 103 and the electronic component leads are disconnected, electrolyte may be drained from cell 370 using valves 234, 410 and 410'. Then the reference and counter electrodes (not shown) may be removed from ports 374 and 376.

At this time any necessary cleaning of generally vertical substrate 103 may be performed. Since the area of the electrolyte opening 380 is substantially less than the entire cross-section of cylinder 372 and since valves 384, 410 and 410' operate to secure most all of the electrolyte inside cell 370 during removal, clean-up of spilled electrolyte is minimal. At this time, any necessary clean up of the areas of generally vertical substrate 103 under securing means 404, 404' can be performed and any coating previously removed from the surface of generally vertical substrate 103 prior to initiating the electrochemical measurement process can be replaced in order to restore generally vertical substrate 103 to its original condition.

Figure 17:
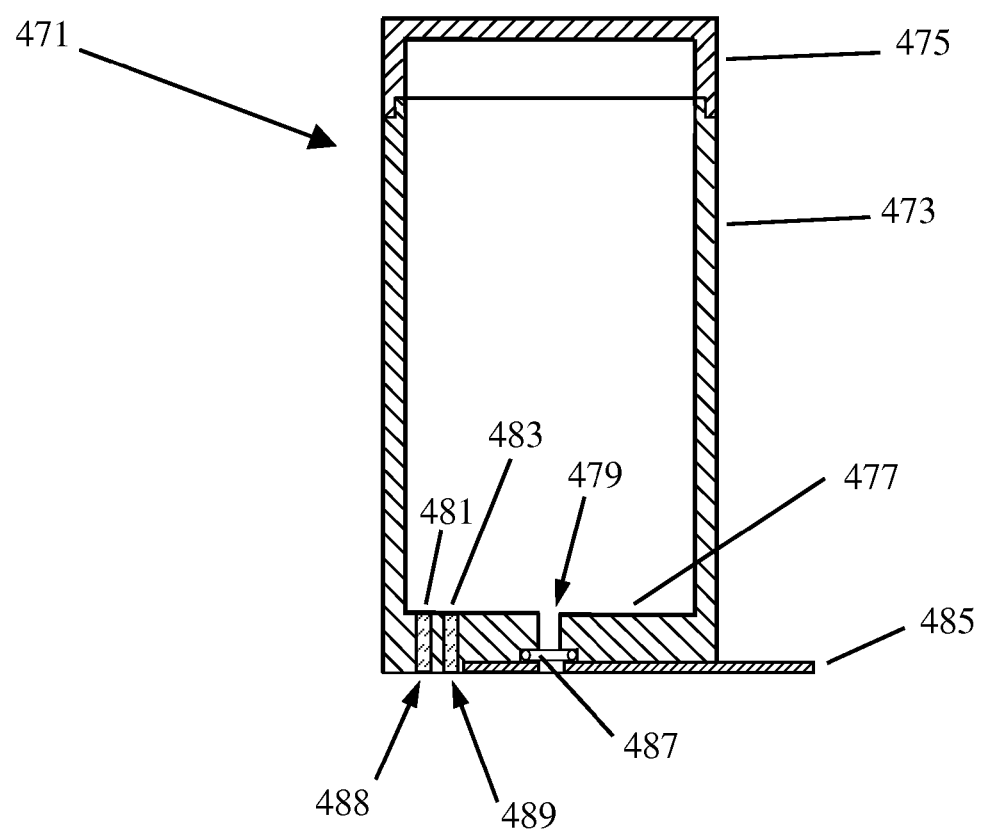
FIG. 17 shows an analytical chamber for use in a further embodiment of the invention shown in FIG. 16.
Figure 18:
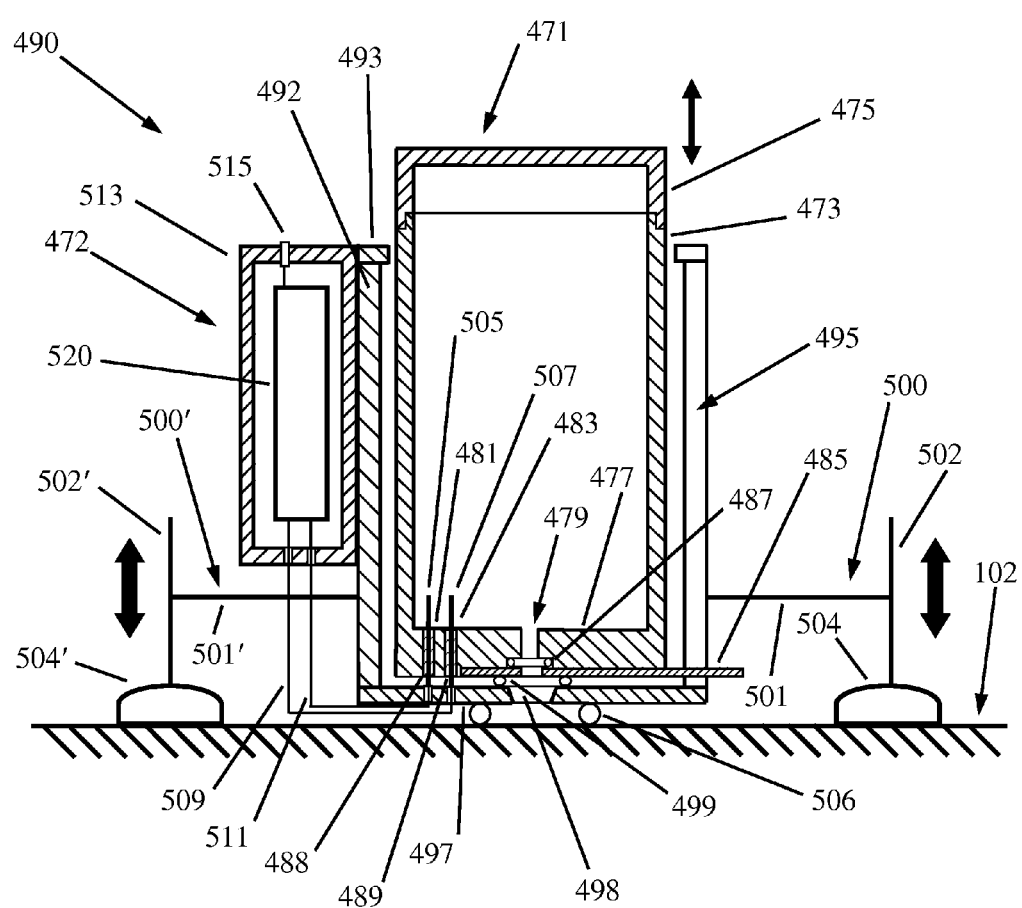
FIG. 18 shows an embodiment of the third modification of the invention with the analytical chamber of FIG. 17 in place.

FIG. 17 illustrates an analytical chamber 471 designed to be used with another embodiment of the electrochemical cell of the invention illustrated in FIG. 18.

The analytical chamber 471 of FIG. 17 comprises a cylinder 473 which is closed at the top end by removable portion 475 and closed at the bottom by plate 477. Plate 477 may be removably secured to the cylinder 473 (not shown) or it may be integral with cylinder 473 as shown. Removable portion 475 is removably secured to cylinder 473 by any suitable means. For example, an O-ring (not shown) could be used to removably secure portion 475 to cylinder 473 or screw threads could be used or any other suitable means. An electrolyte opening 479 is provided in the bottom plate 477. A slide valve 485 is secured to the bottom portion of plate 477 at the external side thereof. Slide valve 485 permits electrolyte opening 479 to be open or closed depending upon the position of slide valve 485. Sealing means 487 is provided between electrolyte opening 479 and slide valve 485 to prevent electrolyte leakage when slide valve 485 is closed. Sealing means 487 may take the form of an O-ring, gasket, releasable adhesive or any other suitable means.

The analytical chamber 471 also has openings 481 and 483 in plate 477. These openings permit a reference electrode (not shown) and a counter electrode (not shown) to penetrate to the interior of analytical chamber 471 when the analytical chamber is inserted into the electrochemical cell 490 shown in FIG. 18

A resealable elastomeric material 488, 488' is placed inside openings 481 and 483 to seal them. This material permits the electrodes to penetrate into the analytical chamber and then seals itself when the electrodes are removed.

This resealable elastomeric material may be similar to the type of material used to seal multi-dose vials in the medical arts. These vials hold multiple doses of medicines which are intended to be injected into a patient. The needle of a hypodermic syringe penetrates the elastomeric material permitting a single dose of the medicine to be withdrawn into the hypodermic syringe and the needle is then withdrawn from the vial. As the needle leaves the elastomeric material, it seals itself.

It is also possible (although not shown in FIG. 17) to use a pressure sensitive adhesive tape to seal openings 481, 483. The tape could cover the electrode openings at the inner or outer surface of plate 477 and thus seal them prior to use. When the reference and counter electrodes penetrate into openings 481 and 483, they will easily puncture the pressure sensitive tape and the cell would be ready to use.

FIG. 18 illustrates another embodiment of the electrochemical cell of the invention. Unlike the previous embodiments this embodiment has a removable analytical chamber. It also has an electronics component similar to the one shown at 50 in FIG. 11 and shown at 420 in FIG. 16.

The electrochemical cell 490 shown in FIG. 18 comprises a separate analytical chamber 471 as shown in FIG. 17 and a base fixture 472. Analytical chamber 471 comprises a cylinder 473 which is closed at the top end by removable portion 475 and closed at the bottom by bottom plate 477. Bottom plate 477 may be removably secured to the cylinder 473 or it may be integral with cylinder 473 as shown. Removable portion 475 is removable secured to cylinder 473 by any suitable means. For example, an O-ring (not shown) could be used to removably secure portion 475 to cylinder 473 or screw threads could be used or any other suitable means. An electrolyte opening 479 is provided in the bottom plate 477. A slide valve 485 is secured to the bottom portion of plate 477 at the external side thereof. Slide valve 485 permits electrolyte opening 479 to be open or closed depending upon the position of slide valve 485. Sealing means 487 is provided between electrolyte opening 479 and slide valve 485 to prevent electrolyte leakage when slide valve 485 is closed. Sealing means 487 may take the form of an O-ring, gasket, releasable adhesive or any other suitable means.

The analytical chamber 471 also has openings 481 and 483 in bottom plate 477. A resealable elastomeric material 488, 488' is placed inside openings 481 and 483 to seal them. This material permits the electrodes to penetrate into the analytical chamber and then seals itself when the electrodes are removed. Openings 481 and 483 permit a reference electrode 505 and a counter electrode 507 to penetrate to the interior of analytical chamber 471 when the analytical chamber is inserted into the base fixture 472 shown in FIG. 18.

Base fixture 472 comprises a cylinder 492 closed at the top end by plate 493 and closed at the bottom by plate 497. Plate 493 has a large opening therein to receive the analytical chamber 471. Bottom plate 497 has an electrolyte opening 498 therein designed to permit electrolyte from the analytical chamber to flow onto the surface of substrate 102. Cylinder 492 has a slot 495 on one side thereof which slot is designed to receive slide valve 485 of analytical chamber 471. The slot extends from the top portion of cylinder 492 to the bottom thereof and extends thru plate 493.

Cylinder 492 has a rod-like reference electrode 505 and a rod-like counter electrode 507 mounted on bottom plate 497. The electrodes extend vertically upwards from bottom plate 497 and are longer than the thickness of bottom plate 477 of analytical chamber 471. The electrodes are positioned on bottom plate 477 so as to be capable of passing through openings 481 and 483 in the bottom of analytical chamber 471 when the analytical chamber is inserted into base fixture 472.

Sealing means 499 is provided on the upper portion of plate 497 and so positioned as to surround the electrolyte opening 479 of analytical chamber 471 and the electrolyte opening 498 of bottom plate 497. Sealing means 499 is also in contact with the bottom of slide valve 485. Sealing means 499 helps to prevent the escape of electrolyte from analytical chamber 471 during operation of electrochemical cell 490.

Sealing means 505 is provided at the external side of plate 487 and surrounds electrolyte opening 498 therein. This permits the cell 490 to be sealed to the surface of substrate 102 in operation. Sealing means 487, 499 and 505 are shown as O-rings but they could easily be any other suitable type of sealing means such as a gasket, etc., etc.

Housing 513 is fastened to cylinder 492 and contains electronics component 520. As noted above, electronics component 520 is similar in design and function to electronics component 50 in FIG. 12 and electronics component 420 in FIG. 16. Electrical connections 509 and 511 connect counter electrode 07 and reference electrode 505, respectively, to electronics component 520. Jack 515 is provided in housing 513 to electrically connect electronics component 520 with the working electrode ((substrate 102).

Electrochemical cell 490 has a mounting means 500, 500' for removably and nondestructively securing the cell to substrate 102. Mounting means 500, 500' comprises a generally horizontal arm 501, 501' which is fastened to cylinder 492. Generally vertical legs 502, 502' ride on the ends of arms 501, 501' and carry securing means 504, 504'. Vertical legs 502, 502' ride up and down on arms 501, 501' so as to permit cell 490 to be biased against one surface of substrate 102. Securing means 504, 504' could be suction cups, magnets, plates with releasable adhesive thereon or any other type of securement means which would permit the cell 490 to be removably and nondestructively secured to substrate 102.

Operation:

Separate analytical chamber 471 would be filled with a suitable electrolyte before use of the cell 490. Analytical chamber 471 could be closed by positioning slide valve 485 to close electrolyte opening 479. Elastomeric seal means 488 and 489 are provided inside openings 481 and 483 to seal them prior to use. When the reference and counter electrodes penetrate into openings 481 and 483, they will easily puncture the elastomeric means 488, 489 and the cell would be ready to use.

Separate analytical chamber 471 could be assembled to base fixture 472 prior to fastening the base fixture 472 to substrate 102 or it could be inserted after the base fixture 472 has been fastened to substrate 102. Once the base fixture 472 has been secured to the surface of substrate 102 by securing means 500, 500', and once analytical chamber 471 has been inserted fully into base fixture 472, the necessary electrical connection between electronics component 520 and the working electrode (substrate 102) may be made using jack 515. Slide valve 485 would be opened to permit electrolyte from the interior of analytical chamber 471 to contact the working electrode (substrate 102) and the necessary electrochemical measurements could be made.

After the desired electrochemical measurements have been taken, slide valve 485 would be closed and the cell 490 removed from the substrate 102. The connection between the electronics component 520 and the working electrode (substrate 102) would be removed and the analytical chamber 471 would be removed from base fixture 472. A fresh analytical chamber 471 could be inserted into base fixture 472 in order to make further electrochemical measurements, as desired.

It is noted that the connection to the working electrode (substrate 102) may be made using springs (not shown) fastened to the bottom of plate 487 and electrically connected to electronics component 520. This would be similar to the springs 34 shown in FIGS. 12 and 13.

Figure 19:
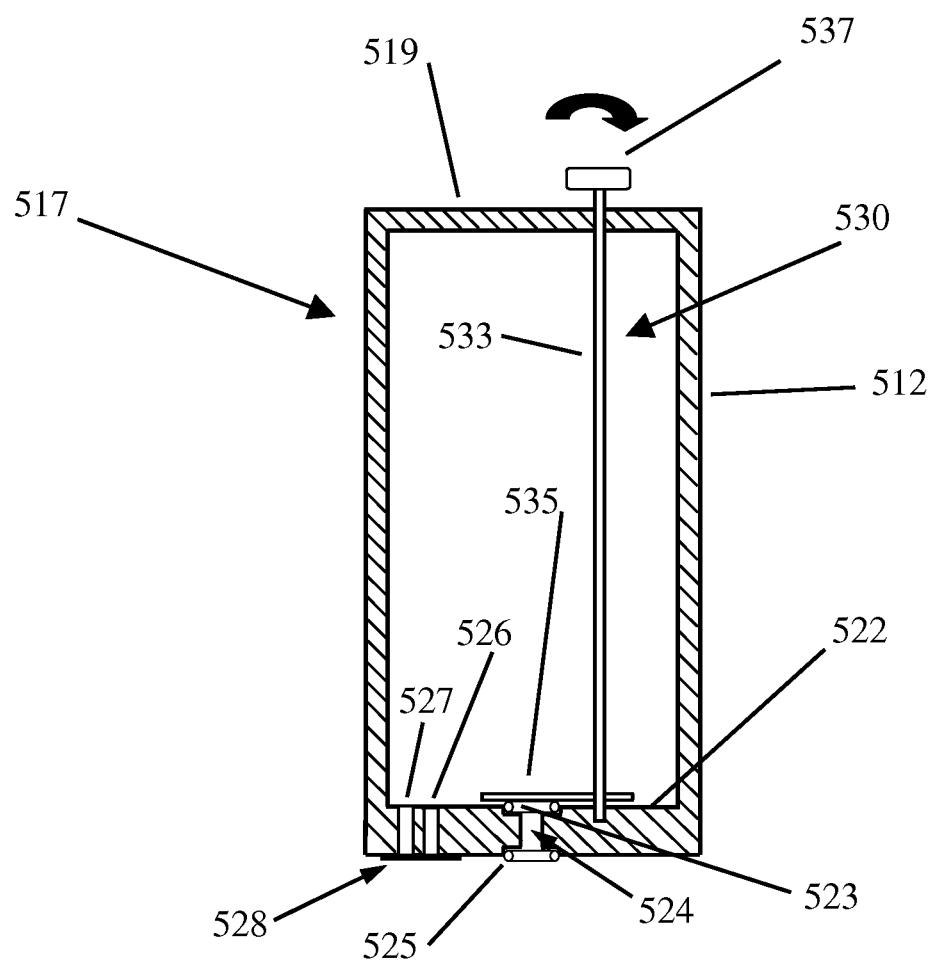
FIG. 19 shows a modification of the analytical chamber shown in FIG. 17.
Figure 20:
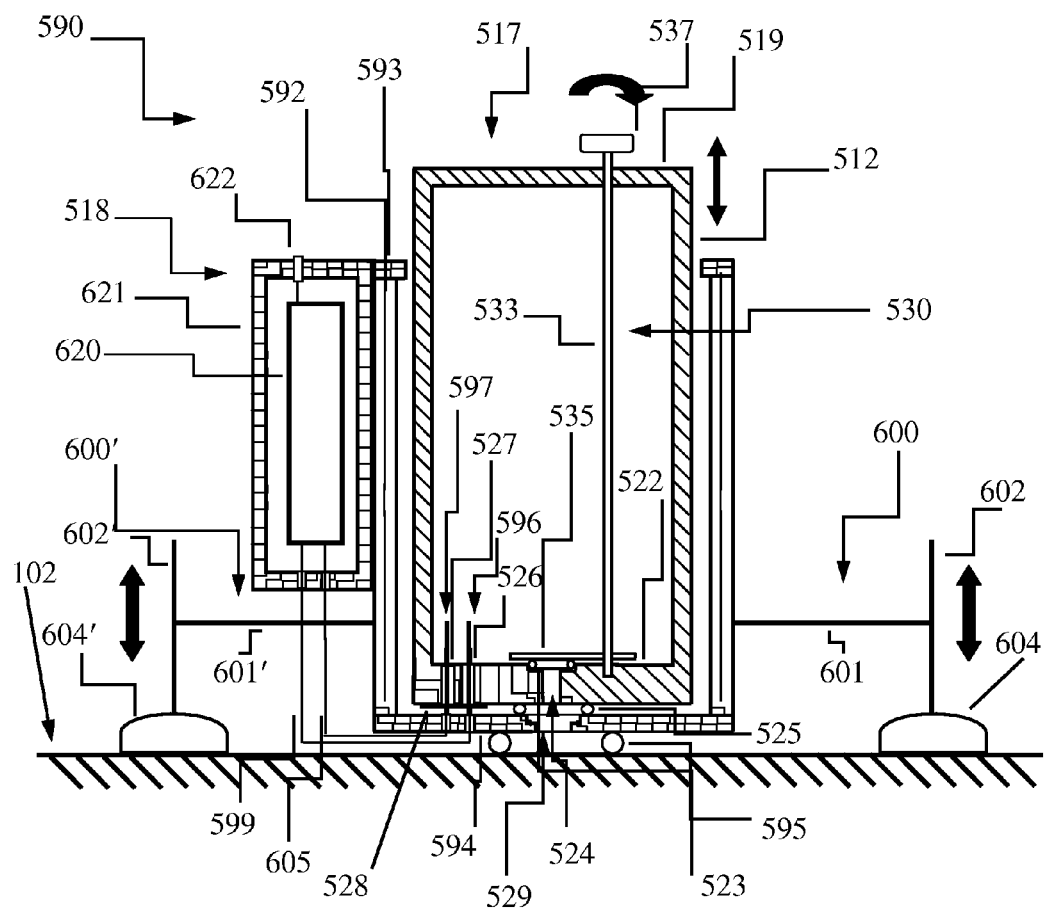
FIG. 20 shows an embodiment of the third modification of the invention using the analytical chamber of FIG. 19.

FIG. 19 illustrates an analytical chamber designed to be used with another embodiment of the electrochemical cell of the invention illustrated in FIG. 20.

The analytical chamber 517 of FIG. 19 comprises a cylinder 512 which is closed at the top end by top plate 519 and closed at the bottom end by bottom plate 522. Plates 519 and 522 may be removably secured to the cylinder 512 (not shown) or they may be integral with cylinder 512 as shown. An electrolyte opening 524 is provided in bottom plate 522. A rotating valve 530 is secured to chamber 517. Rotation of this valve 530 opens or closes electrolyte opening 524 located in bottom plate 522. Rotating valve 530 comprises a rod 533 which penetrates top plate 519 and is rotatable and secured in bottom plate 522. Plate 535 is secured to rod 533 and rotates with rod 533. Knob 537 is provided to permit rotating valve 530 to be rotated. Sealing means 523 is provided at the top of electrolyte opening 524 to prevent electrolyte leakage when rotating valve 530 is closed. Sealing means 525 is provided at the external side of electrolyte opening 524 to seal analytical chamber 517 into the body of the electrochemical measurement means illustrated in FIG.

20. Sealing means 523 and 525 may take the form of an O-ring, gasket, releasable adhesive or any other suitable means.

The analytical chamber 517 also has openings 526 and 527 in bottom plate 522. These openings permit a reference electrode (not shown) and a counter electrode (not shown) to penetrate to the interior of analytical chamber 517 when the analytical chamber is inserted into the electrochemical measurement means shown in FIG. 20

A small strip 528 of pressure sensitive adhesive tape is applied on the exterior side of bottom plate 522 to seal openings 526, 527. Optionally, the pressure sensitive adhesive tape could be applied on the inner surface of bottom plate 522 and thus seal openings 526, 527 prior to use. When the reference and counter electrodes penetrate into openings 526 and 527, they will easily puncture the pressure sensitive adhesive tape and the cell would be ready to use.

An alternate to the strip 528 of pressure sensitive adhesive tape would be to use a resealable elastomeric material inside openings 526 and 527 to seal them. This would be very similar to what is shown in FIG. 17 and described above. This material would permit the electrodes to penetrate into the analytical chamber and then would seal itself when the electrodes are removed.

This resealable elastomeric material may be similar to the type of material used to seal multi-dose vials in the medical arts. These vials hold multiple doses of medicines which are intended to be injected into a patient. The needle of a hypodermic syringe penetrates the elastomeric material permitting a single dose of the medicine to be withdrawn into the hypodermic syringe and the needle is then withdrawn from the vial. As the needle leaves the elastomeric material, it seals itself.

FIG. 20 illustrates another embodiment of the electrochemical cell of the invention similar to that shown in FIG. 18. This embodiment also has a removable analytical chamber and an electronics component similar to the one shown at 50 in FIG. 12 and shown at 420 in FIG. 16.

The electrochemical cell 590 shown in FIG. 20 comprises a separate analytical chamber 517 as shown in FIG. 19 and a base fixture 518. Analytical chamber 517 comprises a cylinder 512 which is closed at the top end by plate 519 and closed at the bottom by bottom plate 522. Bottom plate 522 may be removably secured to the cylinder 512 or it may be integral with cylinder 512 as shown. An electrolyte opening 524 is provided in the bottom plate 522. A rotating valve 530 runs from top plate 519 into the analytical chamber and is secured to the bottom plate 522. Rotating valve 530 comprises a generally vertical rod 533, a bottom flap 535 and a knob 537. Knob 537 permits rod 533 to be rotated causing flap 535 to rotate over the top of electrolyte opening 524 closing the electrolyte opening. This permits electrolyte opening 524 to be open or closed depending upon the position of rotating valve 530. Sealing means 523 is provided between electrolyte opening 524 and bottom flap 535 to prevent electrolyte leakage when rotating valve 535 is closed. Sealing means 523 may take the form of an O-ring, gasket, releasable adhesive or any other suitable means.

The analytical chamber 517 also has openings 526 and 527 in bottom plate 522. A small strip 528 of pressure sensitive tape emplaced on the exterior side of bottom plate 522 covers openings 526, 527 and seals them. These openings permit a reference electrode 597 and a counter electrode 596 to penetrate to the interior of analytical chamber 517 when the analytical chamber is inserted into the base fixture 518. When the electrodes begin to enter openings 526 and 527 they will easily penetrate the strip 528 of pressure sensitive adhesive tape.

Base fixture 518 comprises a cylinder 592 closed at the top end by plate 593 and closed at the bottom by plate 594. Plate 593 has a large opening therein to receive the analytical chamber 517. Bottom plate 594 has an electrolyte opening 529 therein designed to permit electrolyte from the analytical chamber to flow onto the surface of substrate 102.

Cylinder 592 has a rod-like reference electrode 597 and a rod-like counter electrode 596 mounted on bottom plate 522. The electrodes extend vertically upwards from bottom plate 522 and are longer than the thickness of bottom plate 522 of analytical chamber 517. The electrodes are positioned on bottom plate 522 so as to be capable of passing through openings 527 and 526 in the bottom of analytical chamber 517 when the analytical chamber is inserted into base fixture 518.

Sealing means 525 is provided on the upper portion of plate 594 and so positioned as to surround the electrolyte opening 524 of analytical chamber 517 and the electrolyte opening 526 of bottom plate 594. Sealing means 525 helps to prevent the escape of electrolyte from analytical chamber 517 during operation of electrochemical cell 590.

Sealing means 595 is provided at the external side of plate 594 and surrounds electrolyte opening 529 therein. This permits the cell 590 to be sealed to the surface of substrate 102 in operation. Sealing means 523, 525 and 595 are shown as O-rings but they could easily be any other suitable type of sealing means such as a gasket, releasable adhesive or any other suitable means.

Housing 621 is fastened to cylinder 592 and contains electronics component 620. As noted above, electronics component 620 is similar in design and function to electronics component 50 in FIG. 12, electronics component 420 in FIG. 16 and electronics component 520 in FIG. 18 Electrical connections 599 and 605 connect counter electrode 596 and reference electrode 597, respectively, to electronics component 620. Jack 622 is provided in housing 621 to electrically connect electronics component 620 with the working electrode (substrate 102).

Electrochemical cell 590 has a mounting means 600, 600' for removably and nondestructively securing the cell to substrate 102. Mounting means 600, 600' comprises a generally horizontal arm 601, 601' which is fastened to cylinder 592. Generally vertical legs 602, 602' ride on the ends of arms 601, 601' and carry securing means 604, 604'. Vertical legs 602, 602' ride up and down on arms 601, 601' so as to permit cell 590 to be biased against one surface of substrate 102. Securing means 604, 604' could be suction cups, magnets, plates with releasable adhesive thereon or any other type of securement means which would permit the cell 590 to be removably and nondestructively secured to substrate 102.

Operation:

Separate analytical chamber 517 would be filled with a suitable electrolyte before use of the cell 590. Analytical chamber 517 would be closed by using rotating valve 530 to close electrolyte opening 524. The strip 528 of pressure sensitive adhesive tape covers electrode openings 526 and 527 and seals them prior to use. When the reference and counter electrodes penetrate into openings 526 and 527, they will easily puncture the strip 528 of pressure sensitive adhesive tape and the cell would be ready to use.

Separate analytical chamber 517 could be assembled to base fixture 518 prior to fastening the base fixture 518 to substrate 102 or it could be inserted after the base fixture 518 has been fastened to substrate 102. Once the base fixture 518 has been secured to the surface of substrate 102 by securing means 600, 600', and once analytical chamber 517 has been inserted fully into base fixture 518, the necessary electrical connection between electronics component 620 and the working electrode (substrate 102) may be made using jack 622. Rotating valve 530 would be opened to permit electrolyte from the interior of analytical chamber 517 to contact the working electrode (substrate 102) and the necessary electrochemical measurements could be made.

After the desired electrochemical measurements have been taken, rotating valve 530 would be closed and the cell 590 removed from the substrate 102. The connection between the electronics component 620 and the working electrode (substrate 102) would be removed and the analytical chamber 517 would be removed from base fixture 518. A fresh analytical chamber 517 could be inserted into base fixture 518 in order to make further electrochemical measurements, as desired.

It is noted that the connection to the working electrode (substrate 102) may be made using springs (not shown) fastened to the bottom of plate 594 and electrically connected to electronics component 620. This would be similar to the springs 34 shown in FIGS. 12 and 13.

In the embodiment shown in FIG. 18 and FIG. 20 two mounting means are shown attached to the base fixture. In certain environments, one mounting means may be sufficient to properly secure electrochemical cell 490 and 590 to the substrate. It is thought that most situations would require two mounting means. Obviously more than two such mounting means may be used. It is envisaged that three mounting means is the optimal number of mounting means for electrochemical cell 490 and 590, however more than three mounting means may be used if desired and/or necessary. Since each mounting means is individually adjustable, the provision of three mounting means permits the electrochemical cell 490 and 590 to be used on non-planar surfaces. In addition, even though electrochemical cells 490 and 590 have been illustrated as being used to make measurements on generally horizontal surfaces, they could obviously be used to make electrochemical measurements on vertical substrates as well.

Figure 21:
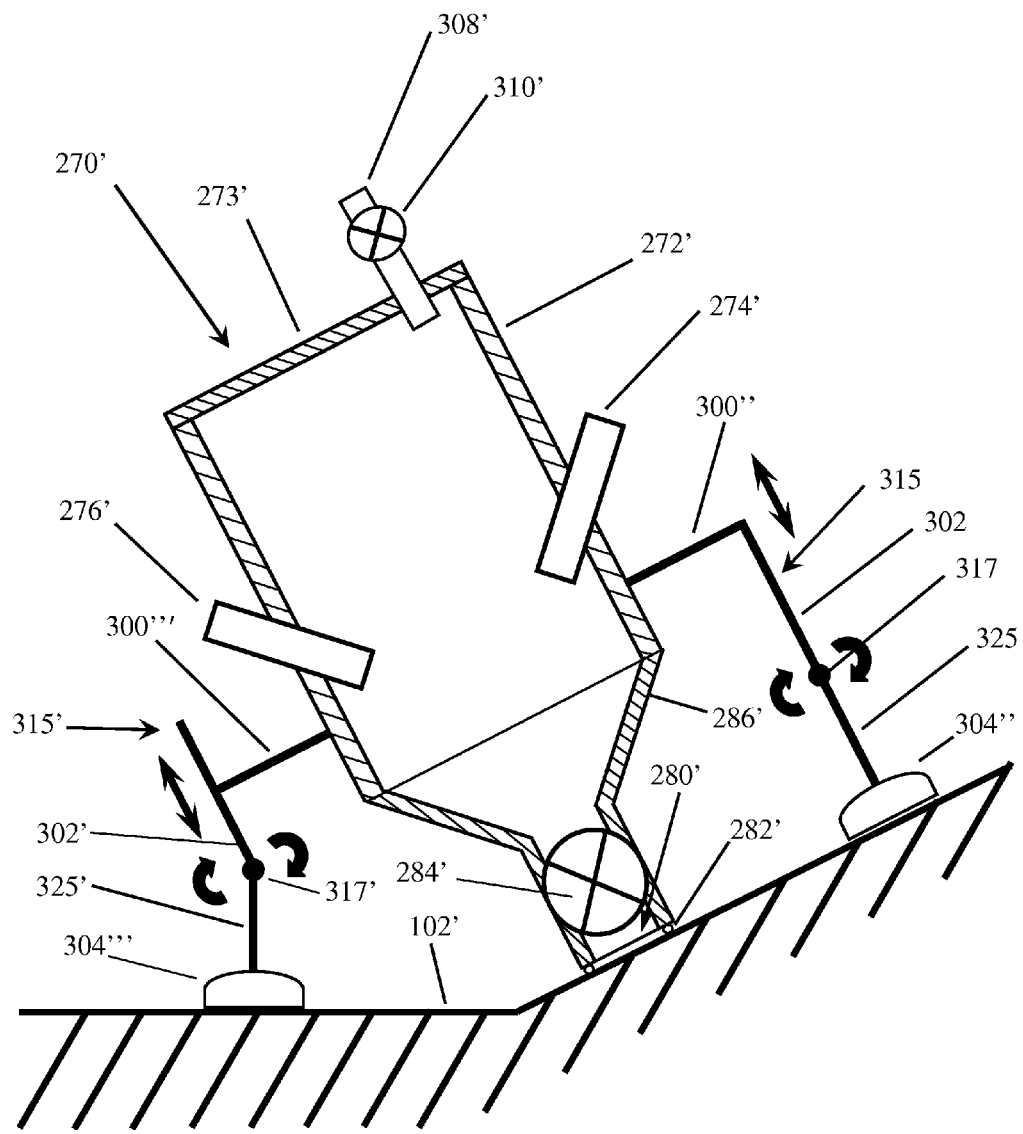
FIG. 21 shows an embodiment of the cell of FIG. 7 wherein the attachment means for biasing the cell towards a substrate has a modification to permit attaching the cell to substrates with widely varying surface morphology, e.g. substrates which are not planar or have an irregular surface

FIG. 21 illustrates another embodiment of the electrochemical cell of the invention similar to that shown in FIG. 7. FIG. 21 shows an embodiment wherein the attachment means for biasing the cell towards a substrate is modified to permit attaching the cell to substrates with widely varying surface morphology, e.g. substrates which are not planar or have an irregular surface. The elements of FIG. 21 that are similar to those in FIG. 7 have similar numbering.

FIG. 21 shows a modification of the electrochemical cell shown in FIG. 7. The electrochemical cell 270' of FIG. 21 comprises a cylinder 272' which is closed at the top end by plate 273' and has a necked-down portion 286' closing its bottom end. Plate 273' and necked-down portion 286' may be removably secured to the cylinder 272' or they may optionally be integral with cylinder 272'. Necked-down portion 286' has an electrolyte opening 280' therein. This electrolyte opening 280' is provided with a sealing means 282' surrounding electrolyte opening 280' at the exterior surface of necked-down portion 286' to seal cell 270' to the surface of substrate 102'. Sealing means 282' may take the form of an O-ring, gasket or any other suitable means.

Ports 274' and 276' are provided for insertion of a reference electrode (not shown) and a counter electrode (not shown). These ports are designed such that the port with an electrode inserted therein would be liquid tight. This could be accomplished, for example, by the use of a plug which held the electrode therein. The plug could be secured and sealed within port 274' and/or 276' using an O-ring, gasket, screw threads or any other suitable means.

Plate 273' has a filling/drain port 308' incorporated therein to permit the cell 270' to be filled with electrolyte. This filling/drain means incorporates a valve 310' to open and/or close port 308'. This will permit the cell 270' to be conveniently emptied of electrolyte when the desired measurements have been taken.

Necked-down portion 286' is provided with a valve 284' near electrolyte opening 280'. This permits the electrolyte opening 280' to be opened or closed. Valve 284' may be a rotary valve, a slide valve or any other suitable type of valve.

At least one mounting means is provided to removably and nondestructively secure cell 270' to a surface of substrate 102'. In this figure two mounting means 315, 315' are shown. Mounting means 315, 315' provide for adjustment of the cell 270' towards and away from substrate 102'. This allows for the electrolyte opening 280' in necked-down portion 286' to be biased against substrate 102' and permits sealing means 282' to seal cell 270' against substrate 102'.

Mounting means 315 and 315' have an attachment arm 300", 300''' which extends generally perpendicular to the longitudinal axis of cylinder 272' and which secures the mounting means to cylinder 272'. In addition mounting means 315, 315' has legs 302, 302' which extend generally perpendicular to attachment arms 300" and 300''' respectively. One end of locking universal joints 317 and 317' are attached to legs 302 and 302'. The other end of locking universal joints 317 and 317' is attached to a first end of leg portions 325 and 325' respectively. Securing means 304", 304''' are attached to the other end of leg portions 325 and 325'. As shown, legs 302 and 302' can move generally perpendicular to arms 300", 300'''. Locking universal joints 317 and 317' permit leg portions 325 and 325' to be independently adjusted to allow securing means 304" and 304''' to secure cell 270 to a substrate with irregular surface morphology. As shown, surface 102' contains a substantial bend. The modified attachment means of this embodiment permits the cell 270' to be securely mounted to this type of irregular surface. Securing means 304", 304''' may comprise a suction cup, a magnet, releasable adhesive means or any other device capable of releasably and nondestructively securing cell 270' to one surface of substrate 102'.

Certain applications may be such that only one mounting means 315 is necessary, however two mounting means 315, 315' are considered necessary in most applications and three mounting means are considered the optimal number for general usage although more may be provided if desired or necessary.

Any suitable type of joining member could be used to join legs 302 and 302' to leg portions 325 and 325' instead of a locking universal joint. The main requirement would be the locking capability and the ability to angularly adjust the legs 302, 302' and leg portions 325, 325'.

Operation:

In operation, substrate 102' would be cleaned as necessary for the desired measurements. This would involve cleaning in the area where securing means 304", 304''' would contact the surface of substrate 102'. In addition, the area of substrate 102' which would be directly under the footprint of electrolyte opening 280' would be cleaned and any coating in this area may have to be removed in order to make the desired electrochemical measurements. Cell 270' would be then be secured to the surface of substrate 102' using mounting means 315, 315'. Mounting means 315, 315' would be adjusted to compliment the morphology of surface 102'. For example, in the situation shown in FIG. 21, the angular orientation of leg portion 325' and leg 302' would be adjusted to permit mounting means 304''' to be securely attached to the left side of substrate 102' [as show] while mounting means 304'' is securely attached to the right side of substrate 102'. Further adjustment of legs 302, 302' in relation to arms 300'' and 300''' may be necessary in order to enable the cell 270' to be securely mounted to substrate 102'.

Once cell 270' has been securely mounted to substrate 102', the remainder of the operation to take an electrochemical measurement with Cell 270' is the same as that described above for cell 270 of FIG. 7. It should be noted that cell 270' is adapted to make electrochemical measurements on horizontal surfaces, sloped surfaces, and even on surfaces that are vertical.

Figure 22:
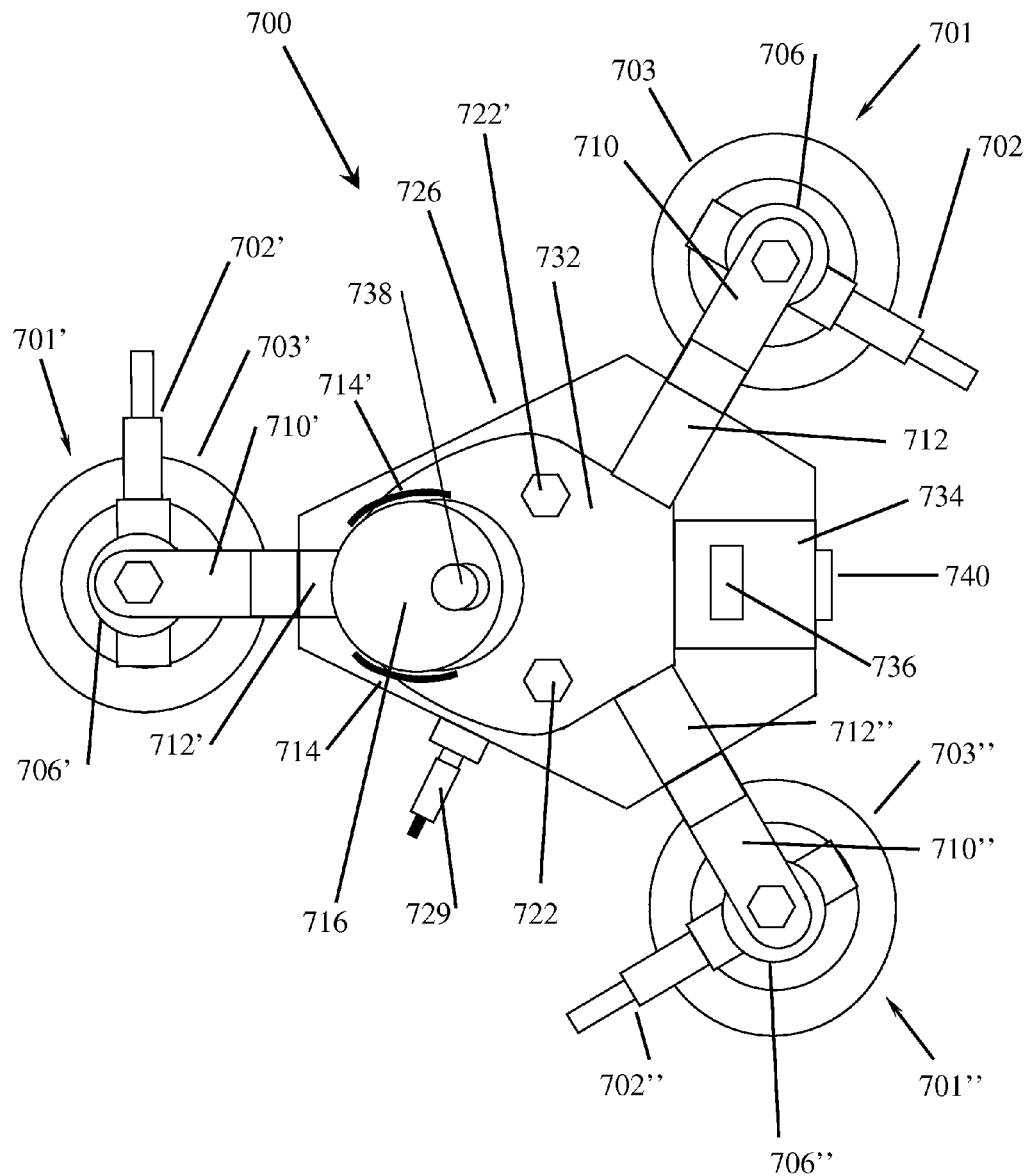
FIG. 22 shows a plan view of an embodiment of the invention utilizing temperature control and a somewhat more flexible attachment means than the attachment means of the first three embodiments.
Figure 23:
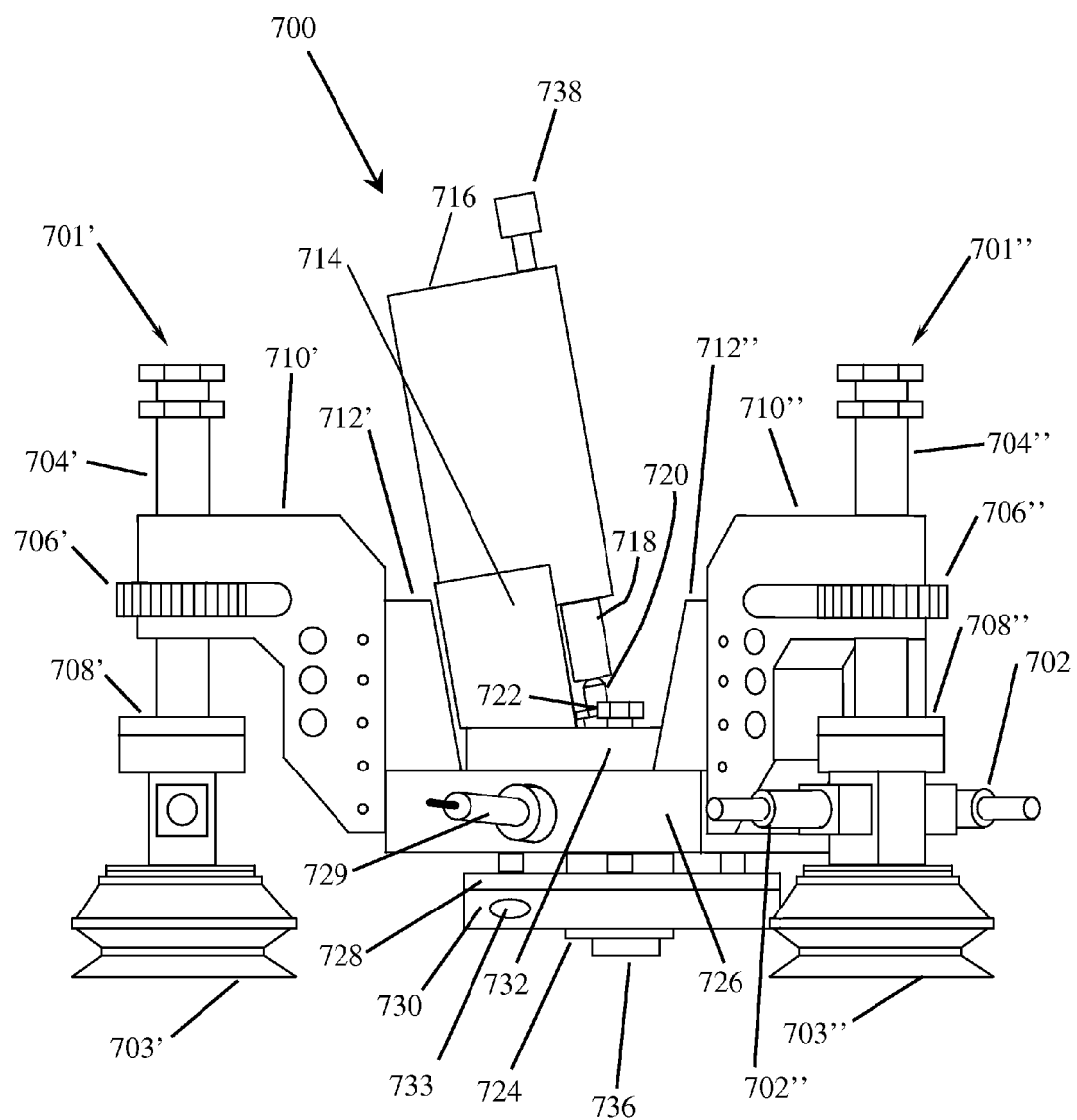
FIG. 23 shows a side view of the embodiment shown in FIG. 22.

FIGS. 22 and 23 show the fifth embodiment of the invention. The structure of electrochemical cell 700 permits accurate temperature control of the electrolyte and of the local substrate area where the electrochemical measurements are being made. This cell also has an attachments means which permits the cell to be secured to substrates with a somewhat irregular surface morphology. It is noted that cell 700 is adapted to make electrochemical measurements on horizontal surfaces, sloped surfaces, vertical surfaces, and even on surfaces that are slightly beyond vertical.

FIG. 22 shows a plan view of cell 700 and FIG. 23 shows a side view of cell 700. These two figures will be described together as they are different views of the same cell with some common components hidden in one view but visible in the other.

Cell 700 comprises a base 726 which is shown with the shape of an irregular hexagon. Obviously, other shapes could be used. Base cover 732 is mounted to the upper portion of base 726. Also mounted to base 726 are leg base mounts 712, 712' and 712''. These leg base mounts provide the mounting means for the suction cup assemblies 701, 701' and 701''.

Each suction cup assembly comprises a large bellows-type pneumatic suction cup 703, 703' and 703'' with a coaxial venturi 702, 702' and 702'' mounted to the upper portion thereof. Venturi mount assemblies 708, 708' and 708'' attach coaxial venturis 702, 702' and 702'' to adjustment screws 704, 704' and 704''. Adjustment screws 704, 704' and 704'' are carried in adjustment screw mounts 710, 710' and 710''. Adjustment nuts 706, 706' and 706'' permit fine height adjustment of adjustment screws 704, 704' and 704'' with respect to the adjustment screw mounts 710, 710' and 710''.

Adjustment screw mounts 710, 710' and 710'' are attached to base 726 by leg base mounts 712, 712' and 712''. The means attaching the adjustment screw mounts to the leg base mounts permits a coarse height adjustment of adjustment screw mounts 710, 710' and 710'' with respect to the leg base mounts 712, 712' and 712'' as will be further described below.

Electronics component 734 is attached to base 726 between suction cup assemblies 701 and 701''. This electronics component comprises a miniature potentiostat similar to electronics component 50 shown and described above with respect to FIGS. 12 and 14. Digital display 736 is similar to digital display 54 described above and shown in FIG. 11. Electronics component 734 may also comprise temperature control circuitry whose function will be further discussed below. In addition, electronics control 734 may interact with one or more electro-mechanical interlock switches as described below.

Electrolyte tank 716 is mounted to cell 700 at a slight angle to the vertical to avoid problems with air bubbles in the electrolyte solution in the electrochemical analytical chamber 724 which will be further described below. The particular angle shown in FIGS. 22 and 23 is 10° from the vertical although other angles obviously may be suitable. Electrolyte tank 716 is connected to base cap 732 by quick-disconnect fittings 718 and 720 and positioned on base cap 732 by means of fluid tank base 714, 714'. Fluid tank base 714, 714' is mounted on base cap 732 and comprises a curved wing on each side which receives the outer portion of fluid tank 716.

Figure 27:
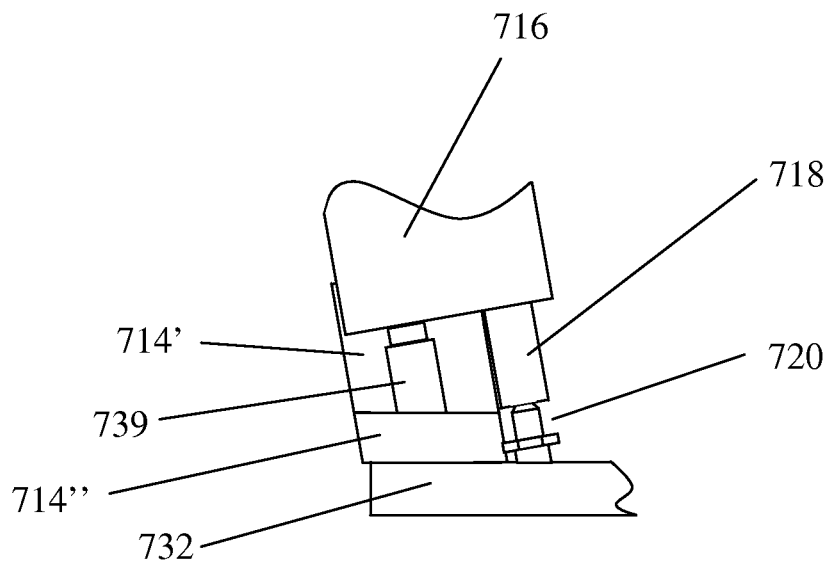
FIG. 27 shows details of the structure for mounting the electrolyte tank shown in FIGS. 22 and 23 to the electrochemical cell.

As shown in FIG. 27, an electro-mechanical interlock switch 739 is mounted on shelf 714'' which connects wings 714, 714'. Electro-mechanical interlock switch 739 prevents operation of electrochemical cell 700 if the electrolyte tank 716 is not properly mounted to base 726 by means of quick-disconnect fittings 718 and 720. The electro-mechanical interlock switch may control circuitry in electronics component 734 to prevent operation of cell 700 when electrolyte tank 716 is not properly positioned on the fluid tank base 714,714'. Electrolyte tank 716 is vented at the top portion thereof by vent means 738.

Reference electrode 729 is mounted on one side of base 726 and slightly angled downwards from the horizontal. This is to avoid problems with air bubbles in the electrochemical analytical chamber 724 which will be discussed further below.

An important feature of the invention is control of the temperature of the substrate surface where the electrochemical measurements are being taken. Another important feature of the invention is control of the electrolyte solution temperature. It is well-known that the rate of almost every chemical reaction is dependent upon the temperature of the reactants. It is also true that the rate of electrochemical reactions is, in like manner, dependent upon the temperature of the reactants. It has been discovered that, by eliminating the influence of temperature on the reaction rate, more consistent and reliable results can be obtained when making electrochemical measurements with the electrochemical cells disclosed herein.

With this in mind, the electrochemical cell of the invention has a means to control the temperature of the substrate of interest in the area where the electrochemical measurements are being made and a means to control the temperature of the electrolyte solution. It is noted that the embodiments disclosed herein all use heating means to control the temperature of the local substrate area and the electrolyte; however, it is recognized that some situations might call for a cooling means to control these temperatures.

The temperature control features of the instant invention involve the use of heating elements in thermal contact with the substrate of interest near the area where the electrochemical measurements are being made and with the electrolyte solution. Each of these temperature control features will be further discussed below.

While some previous embodiments have been designed such that all power necessary for operation of the cell is provided by an on-board battery, this embodiment requires substantially greater amounts of power for the temperature control mechanisms. To this end, it is envisaged that external power will be supplied via connector 740 [shown in FIG. 22] when cell 700 is in operation. In addition, this embodiment requires compressed air to power the coaxial venturi assemblies 702, 702' and 702'' in order to provide a vacuum in suction cup assemblies 701, 701' and 701''.

The temperature control means for the substrate of interest is heating pad 730. Heating pad 730 is a large annular heater which is mounted to the lower surface of base 726 by annular heater pad mount 728. Heating pad 730 and heater pad mount 728 surround analytical chamber 724. Heating pad 730 has a resistive temperature device [RTD] 733 or another suitable temperature measurement device embedded therein or attached thereto to shut down operation of heating pad 730 when a predetermined maximum temperature is exceeded. Hex adjustment screws 722 and 722' permit the heater pad mount 728 and thus heating pad 730 to be moved towards or away from base 726. Analytical chamber 724 has a gasket 736 mounted to the lower end thereof which gasket serves to seal the analytical chamber to the substrate of interest when electrochemical measurements are being made. Analytical chamber 724 is shown in FIG. 23 as extending slightly below the lower surface of heating pad 730. However, in normal operation of cell 700 this would not be the case as heating pad 730 would have been lowered to contact the surface of the substrate of interest prior to taking any electrochemical measurements. Analytical chamber 724 will be further described below.

Figure 24:
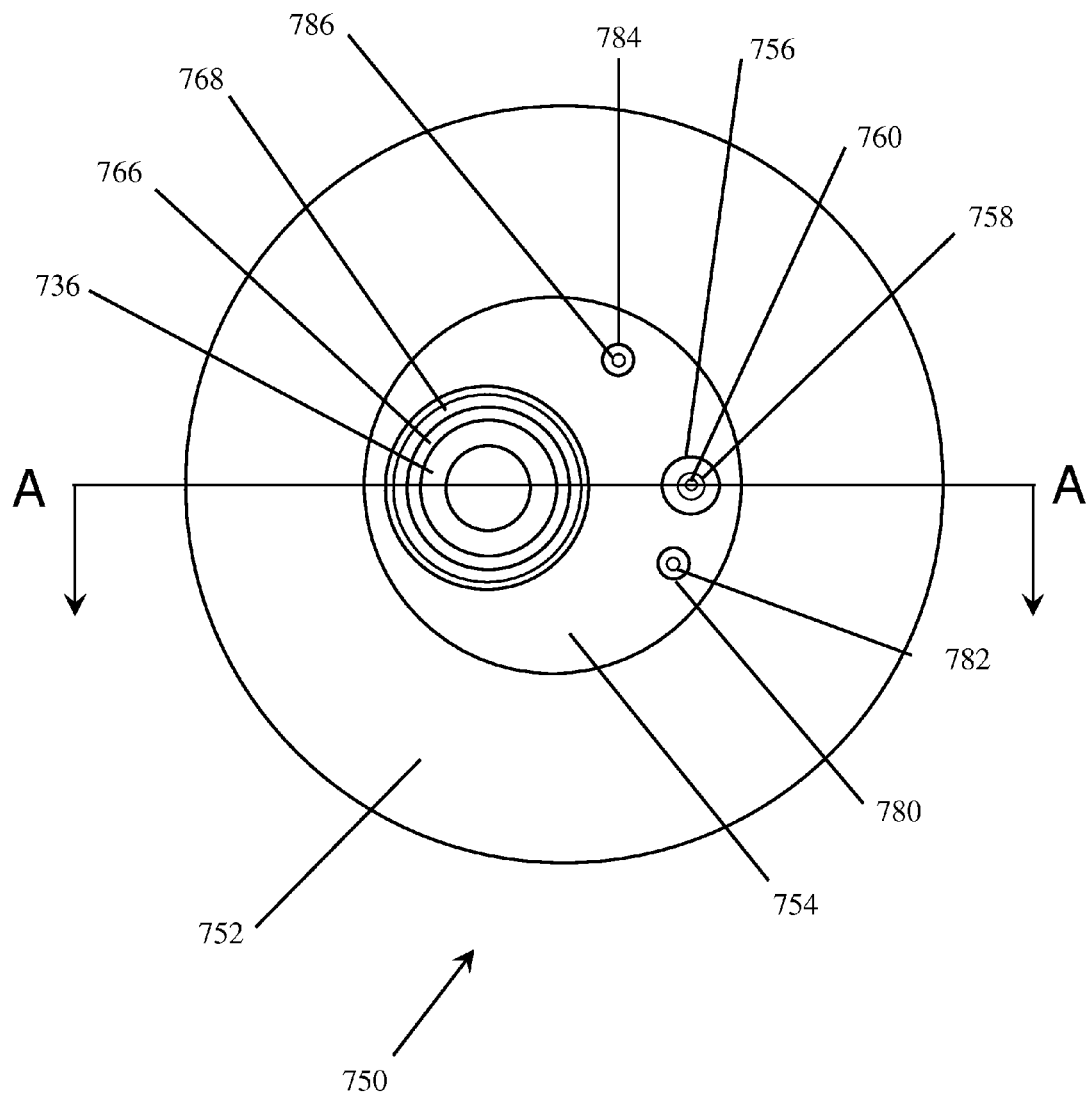
FIG. 24 shows a bottom view of the test fluid housing with the analytical chamber inserted therein.
Figure 25:
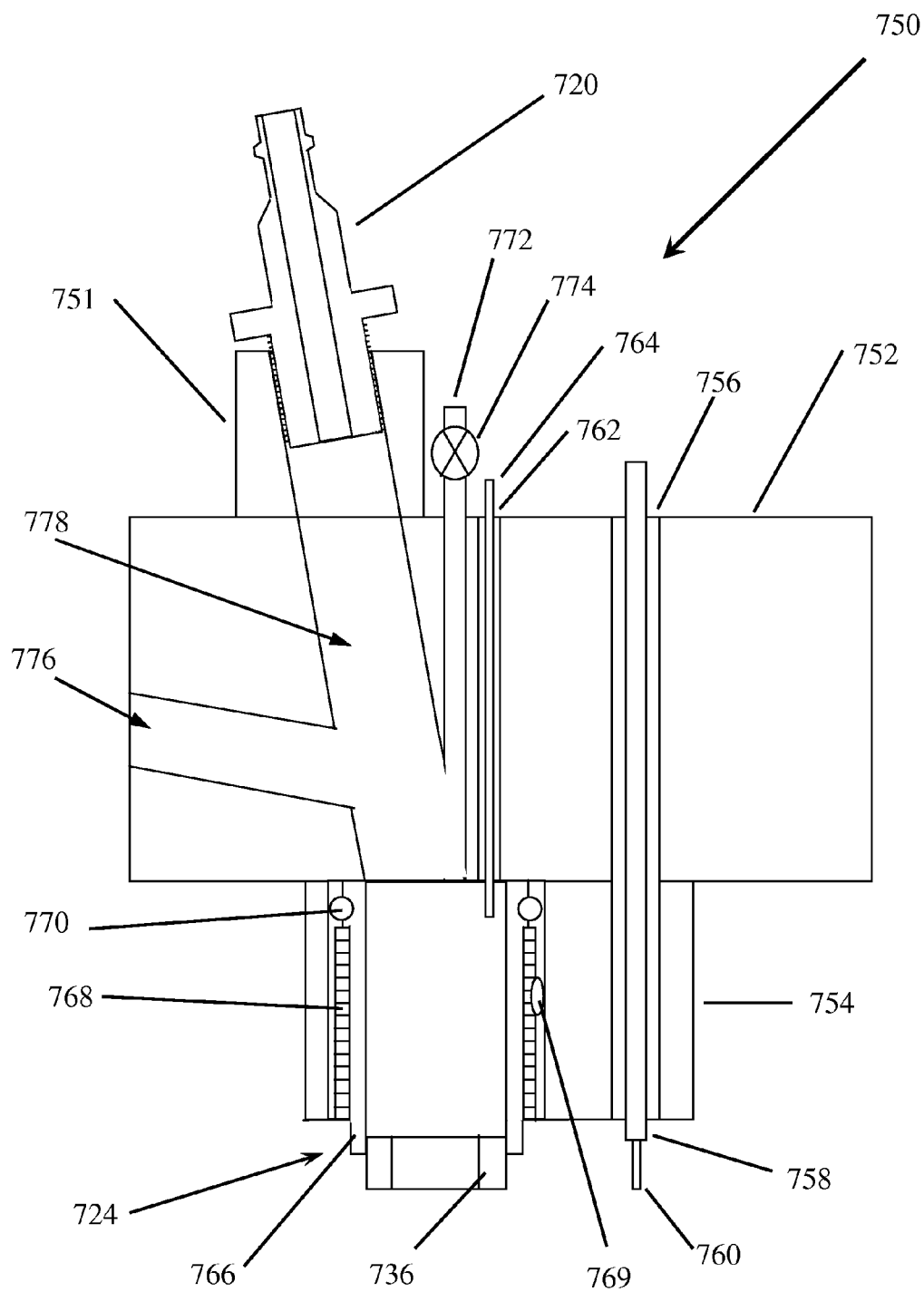
FIG. 25 shows a cross section of the test fluid housing along section line A-A of FIG. 24.

FIG. 24 shows a bottom view of test fluid housing 750. FIG. 25 shows a cross-section view of test fluid housing 750 along section A-A of FIG. 24. These two figures will be described together as they are different views of the same elements with some common components hidden in one view but visible in the other. It is noted that test fluid housing 750 is primarily contained within base 726 with portions thereof extending into base cap 732 and below base 726.

Test fluid housing 750 comprises three cylindrical portions, 751, 752 and 754 made of a polymeric material. Test fluid housing portion 752 has the smallest portion 751 mounted to its upper surface. Portion 754 is intermediate in size between portions 751 and 752 and is mounted to the lower surface of test fluid housing portion 752. Quick-disconnect fitting 720 is mounted to test fluid housing portion 751. Electrolyte fluid feed bore 778 starts in portion 751 and extends through portion 752 to analytical chamber 724 which is contained within test fluid housing portion 754 as shown in FIG. 25. A reference electrode bore 776 for mounting reference electrode 729 [shown in FIG. 23] extends from an outer surface of portion 752 to intersect electrolyte fluid feed bore 778. A vent pipe 772 extends from the upper surface of portion 752 to intersect electrolyte fluid feed bore 778 at the lower portion thereof as shown in FIG. 25. Vent pipe 772 has a valve 774 in the upper portion thereof to allow gas to escape from the analytical chamber 724, from the reference electrode bore 776 and from the electrolyte fluid feed bore 778. During operation of cell 700, vent pipe 772 prevents gas bubbles in the electrolyte fluid from interfering with accurate electrochemical measurements. This feature is important because cell 700 can be used to make electrochemical measurements on substrates with many different orientations from generally horizontal to vertical and even to somewhat past vertical.

Analytical chamber 724 as noted above is mounted within test fluid housing portion 754. Chamber 724 comprises a passive metallic cylinder 766 which is surrounded by a heating coil 768 and has a gasket 736 extending from the lower portion thereof. Heating coil 768 has a resistive temperature device [RTD] 769 or another suitable temperature measurement device embedded therein or attached thereto to shut down operation of heating coil 768 when a predetermined maximum temperature is exceeded.

The passive metallic cylinder 766 serves as a counter electrode when making electrochemical measurements with cell 700.

The purpose of gasket 736 is to seal analytical chamber 724 to the substrate of interest. Stainless steel is an example of a passive metal which is very suitable for the cylinder 766 although other passive metals may be used which would be suitable chambers for the specific types of electrochemical measurements desired. O-ring 770 is placed around the upper portion of cylinder 766 to seal analytical chamber 724 and to prevent electrolyte contact with heating coil 768. Bore 762 is provided in test fluid lousing portion 752 to permit resistive thermal device [RTD] 764 or another suitable temperature-measuring device to access the electrolyte within analytical chamber 724. The RTD 764 [or other suitable temperature measurement device] permits the electronics component 734 to control the electrolyte fluid temperature by controlling the operation of heating coil 768.

Bore 756 extends through test fluid housing portions 752 and 754 to permit an electro-mechanical interlock device 758 to access the substrate of interest when cell is in operation. Spring loaded contact 760 is contained within the bottom portion of electro-mechanical interlock device 758. In operation, the electro-mechanical interlock device 758 may control circuitry in electronics component 734 to prevent operation of cell 700 when spring loaded contact 760 is not depressed by the substrate as it would be when cell 700 is properly mounted on the substrate of interest.

Bores 780 and 784 [shown in FIG. 24] also extend through test fluid housing portions 752 and 754. Bore 780 permits working electrode probe 782 to make electrical contact with the working electrode which is the substrate of interest upon which the electrochemical measurements are being made. Bore 784 permits RTD 786 [or another suitable temperature measurement device] to measure the temperature of the working electrode [the substrate of interest]. This connection permits electronics component 734 to control the temperature of the substrate within the measurement area by controlling the operation of heating pad 730 [shown in FIG. 23].

Figure 26:
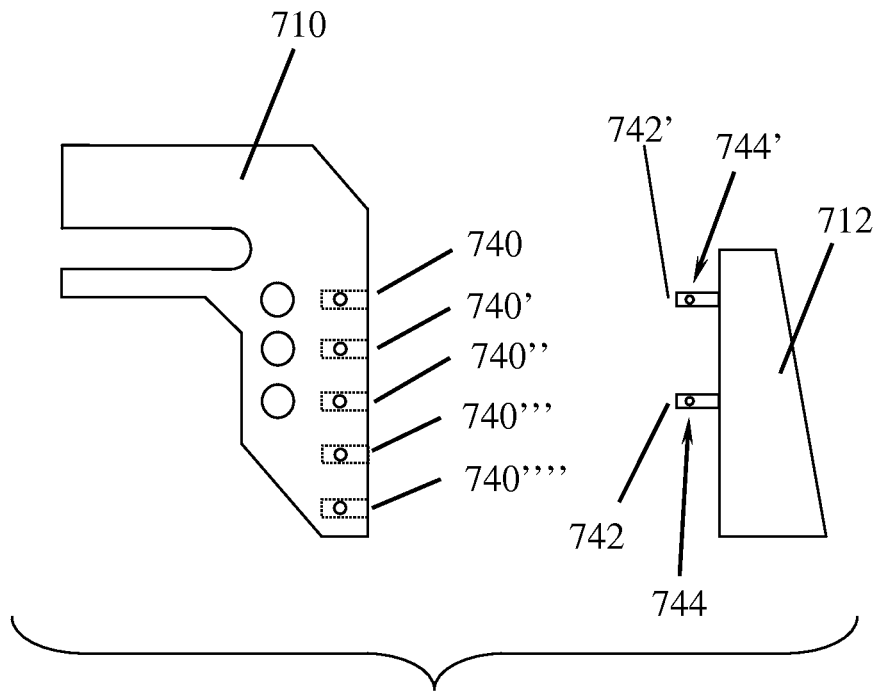
FIG. 26 shows details of a coarse height adjustment for the electrochemical cell of FIGS. 22 and 23.

FIG. 26 shows the means which attaches adjustment screw mount 710 to leg base mount 712 and provides a coarse height adjustment as discussed above. Obviously, similar means are provided to attach adjustment screw mounts 710' and 710" to leg base mounts 712' and 712". In FIG. 26 adjustment screw mount 710 is shown with five linearly spaced holes 740, 740', 740", 740''' and 740'''' bored into the right side of adjustment screw mount 710. Each hole 740, 740', 740", 740''' and 740'''' has a smaller perpendicular hole bored there through to permit a push pin [not shown] to be inserted into the holes.

Leg base mount 712 has a corresponding set of linearly spaced holes [not shown] bored therein. Pins 742, 742' are removably secured in two of the corresponding holes in leg base mount 712. Pins 742 and 742' have transverse bores 744 and 744' there through. In operation, leg base mount 712 would be assembled to adjustment screw mount 710 with pins 742, 742' being inserted into corresponding holes 740 and 740" in adjustment screw mount 710. When assembled, the perpendicular holes in adjustment screw mount 710 align with the transverse bores 744, 744' of pins 742, 742'. Push pins [not shown] are inserted through the aligned perpendicular holes and transverse bores 744, 744' to secure the assembly. In order to adjust the relative vertical position of adjustment screw mount 710 and leg base mount 712, the push pins would be removed, adjustment screw mount 710 and leg base mount 712 would be separated, and pins 742 and 742' could then be inserted into different holes, for example 740' and 740'''. This would give a different relative position between adjustment screw mount 710 and leg base mount 712. In addition, pins 742, 742' could be removed from their holes in leg base mount 712 and placed in other holes achieve different relative positioning of adjustment screw mount 710 and leg base mount 712.

Operation:

Once the substrate surface is suitably prepared, cell 700 is positioned such that the analytical chamber 724 is over the substrate area of interest and the suction cup assemblies 701, 701' and 701" are positioned on the substrate surface.

Compressed air from a suitable source [not shown] is provided to each of the coaxial venturi assemblies 702, 702' and 702" allowing the suction cup assemblies 701, 701' and 701" to secure cell 700 to the substrate surface. The construction of suction cups 703, 703' and 703" and the independent height adjustment at each suction cup permit the cell to be secured to a substrate surface that is moderately irregular, e.g. not planar or a moderately rough surface.

The distance between analytical chamber 724 and the substrate surface is adjusted to the optimal distance for a good seal between the analytical chamber 724 and the substrate surface using the coarse height adjustments means illustrated in FIG. 26 and/or using the fine height adjustment provided by adjustment nuts 706, 706' and 706". The heater pad 730 will then be adjusted, as necessary, via hex adjustment screws 722 and 722'. Heater pad 730 should then be in close contact with the substrate surface. It is noted that heater pad 730 is somewhat flexible to allow for a suitable thermal connection to moderately irregular surfaces. Electrical connections [using a cable, not illustrated] are made between the reference electrode 729 and the electronics component 734. Electrical power from an external source is provided to cell 700 via connector 740.

A full electrolyte tank 716 is connected to cell 700 via quick-disconnect fittings 718 and 720. Wings 714, 714' guide electrolyte tank 716 into place and the bottom end of electrolyte tank 716 contacts electro-mechanical interlock switch 739 when the tank is fully seated. Power is applied to the heating pad 730 and heating coil 768, as necessary, to assure that the electrolyte fluid and the substrate surface area of interest achieve the optimum temperature. Once the optimum temperatures are achieved, electronics component 734 will make and store the desired electrochemical measurements.

Figure 28:
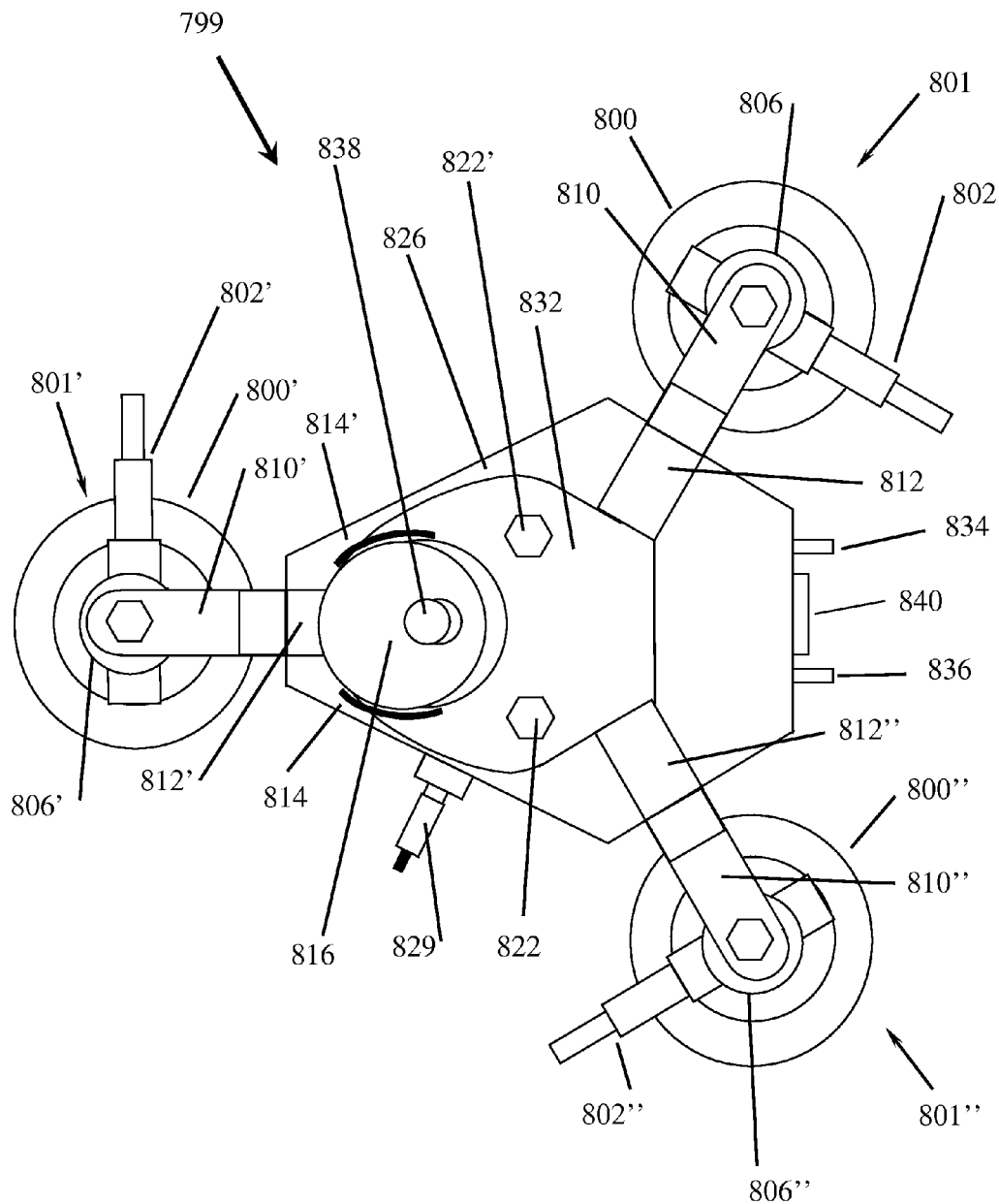
FIG. 28 shows a modification of the embodiment of the cell of FIGS. 22 and 23, which eliminates the self-contained miniature potentiostat.

FIG. 28 shows the sixth embodiment of the invention. Cell 799 similar to the construction of cell 700 shown in FIGS. 22 and 23 but without the electronics component 734 of cell 700. Cell 799 is designed to be connected to an external potentiostat [not shown] and external circuitry which would control the analytical chamber heating elements and the heating pad.

The structure of electrochemical cell 799 also permits accurate temperature control of the electrolyte and of the local substrate area where the electrochemical measurements are being made. This cell also has an attachments means which permits the cell to be secured to substrates with a somewhat irregular surface morphology. It is noted that cell 799 is adapted to make electrochemical measurements on horizontal surfaces, sloped surfaces, vertical surfaces, and even on surfaces that are slightly beyond vertical.

Cell 799 comprises a base 826 which is shown with the shape of an irregular hexagon. Obviously, other shapes could be used. Base cover 832 is mounted to the upper portion of base 826. Also mounted to base 826 are leg base mounts 812, 812' and 812". These leg base mounts provide the mounting means for the suction cup assemblies 801, 801' and 801".

Each suction cup assembly comprises a large bellows-type pneumatic suction cup 800, 800' and 800" with a coaxial venturi 802, 802' and 802" mounted to the upper portion thereof. Coaxial venturis 802, 802' and 802" are mounted to the upper portion of suction cups 800, 800' and 800". Venturi mount assemblies which are not shown in FIG. 28 but which are similar to venturi mount assemblies 708, 708' and 708" of FIG. 23 attach to adjustment screws which also are not shown in FIG. 28 but which are similar to adjustment screws 704, 704' and 704" shown in FIG. 23. These adjustment screws are carried in adjustment screw mounts 810, 810' and 810". Adjustment nuts 806, 806' and 806" permit fine height adjustment of the adjustment screws with respect to the adjustment screw mounts 810, 810' and 810".

Adjustment screw mounts 810, 810' and 810" are attached to base 826 by leg base mounts 812, 812' and 812". The means attaching the adjustment screw mounts to the leg base mounts permits a coarse height adjustment of adjustment screw mounts 810, 810' and 810" with respect to the leg base mounts 812, 812' and 812" in the same manner as shown in FIG. 26.

Electrolyte tank 816 is mounted to cell 799 at a slight angle to the vertical to avoid problems with air bubbles in the electrolyte solution as discussed above with respect to FIGS. 22 and 23. Electrolyte tank 816 is connected to base cap 832 by quick-disconnect fittings not shown in FIG. 28 but which are similar to quick disconnect fittings 718 and 720 shown in FIG. 23. Electrolyte tank 816 is positioned on base cap 832 by means of fluid tank base 814, 814'. Fluid tank base 814, 814' is mounted on base cap 832 and comprises a curved wing on each side which receives the outer portion of fluid tank 816.

An electro-mechanical interlock switch is mounted on a shelf portion of fluid tank base 814,814'. Neither the interlock switch or shelf portion is shown in FIG. 28 but they are identical to the showing in FIG. 27. As shown in FIG. 27, an electro-mechanical interlock switch 739 is mounted on shelf 714" which connects wings 714, 714'. Electro-mechanical interlock switch 739 prevents operation of electrochemical cell 700 if the electrolyte tank 716 is not properly mounted to base 726 by means of quick-disconnect fittings 718 and 720. The interlock switch of cell 799 operates in the same manner as that shown in FIG. 27. This electro-mechanical interlock switch controls circuitry in an external electronics package [not shown] to prevent operation of cell 799 when electrolyte tank 816 is not properly positioned on the fluid tank base 814,814'. Electrolyte tank 816 is vented at the top portion thereof by vent means 836.

Reference electrode 829 is mounted on one side of base 826 and slightly angled downwards from the horizontal. This is to avoid problems with air bubbles as discussed above in regard to FIGS. 22 and 23.

An important feature of the invention is control of the temperature of the substrate surface where the electrochemical measurements are being taken. Another important feature of the invention is control of the electrolyte solution temperature. It is well-known that the rate of almost every chemical reaction is dependent upon the temperature of the reactants. It is also true that the rate of electrochemical reactions is, in like manner, dependent upon the temperature of the reactants. It has been discovered that, by eliminating the influence of temperature on the reaction rate, more consistent and reliable results can be obtained when making electrochemical measurements with the electrochemical cells disclosed herein.

With this in mind, the electrochemical cell of the invention has a means to control the temperature of the substrate of interest in the area where the electrochemical measurements are being made and a means to control the temperature of the electrolyte solution. It is noted that the embodiments disclosed herein all use heating means to control the temperature of the local substrate area and the electrolyte; however, it is recognized that some situations might call for a cooling means to control these temperatures.

The temperature control features of the instant invention involve the use of heating elements in thermal contact with the substrate of interest near the area where the electrochemical measurements are being made and with the electrolyte solution. Each of these temperature control features will be further discussed below.

The temperature control means for cell 799 is identical to the temperature control means for cell 700 except that it is achieved with external control circuitry [not shown] instead of an onboard electronics component. Thus the temperature of the substrate of interest is controlled by a heating pad identical to heating pad 730 shown in FIG. 23. The heating pad is a large annular heater which is mounted to the lower surface of base 826 by annular heater pad mount not shown in FIG. 28 but identical to heater pad mount 728 shown in FIG. 23. The heating pad and heater pad mount surround the analytical chamber and have hex adjustment screws 822 and 822' permit the heater pad mount and thus heating pad to be moved towards or away from base 826 as described and shown above with respect to FIG. 23 and cell 700.

Reference electrode 829 is mounted to base 826 in the same manner as reference electrode 729 is mounted to base 726 for cell 700 described above and shown in FIG. 23.

Since cell 799 does not have an on-board electronics component, plugs 834, 836 and 840 provide electrical connection between the electrodes, the temperature control devices and interlocks and the heating elements of cell 799 and the external control means. They also provide for a source of external power for the heating pad and the heating coil.

Operation:

Once the substrate surface is suitably prepared, cell 799 is positioned such that the analytical chamber is over the substrate area of interest and the suction cup assemblies 801, 801' and 801" are positioned on the substrate surface.

Compressed air from a suitable source [not shown] is provided to each of the coaxial venturi assemblies 802, 802' and 802" allowing the suction cup assemblies 801, 801' and 801" to secure cell 799 to the substrate surface. The construction of suction cups 800, 800' and 800" and the independent height adjustment at each suction cup permit the cell to be secured to a substrate surface that is moderately irregular, e.g. not planar or a moderately rough surface.

The distance between the analytical chamber and the substrate surface is adjusted to the optimal distance for a good seal between the analytical chamber and the substrate surface using the coarse height adjustments means illustrated in FIG. 26 and/or using the fine height adjustment provided by adjustment nuts 806, 806' and 806". The heater pad will then be adjusted, as necessary, via hex adjustment screws 822 and 822'. The heater pad should then be in close contact with the substrate surface. It is noted that the heater pad is somewhat flexible to allow for a suitable thermal connection to moderately irregular surfaces. Electrical connections [using cables, not illustrated] are made between the reference electrode 829, connectors 834, 836 and 840 and the external electronics [not shown]. The external electronics would comprise a control system and a potentiostat. Electrical power from an external source is provided to cell 799 via connector 840.

A full electrolyte tank 816 is connected to cell 799. Wings 814, 814' guide electrolyte tank 816 into place and the bottom end of electrolyte tank 816 contacts an electromechanical interlock switch [not shown] when the tank is fully seated. Power is applied to the heating pad and heating coil, as necessary, to assure that the electrolyte fluid and the substrate surface area of interest achieve the optimum temperature. Once the optimum temperatures are achieved, the external electronics will make and store the desired electrochemical measurements.

The invention claimed is:

1. A compact and portable electrochemical cell for making electrochemical measurements on the surface of a substrate of indefinite size comprising:
   A. an analytical chamber with a top and a bottom end;
   B. sealing means associated with the bottom end of said chamber to seal said bottom end to one surface of a substrate of indefinite size;
   C. means to mount a counter electrode in said analytical chamber;
   D. means to mount a reference electrode in said analytical chamber;
   E. securing means to removably and nondestructively secure said bottom end of said analytical chamber against one surface of a substrate of indefinite size, said securing means further comprising adjustment means to adjust the distance between said analytical chamber toward the surface of a substrate of indefinite size; and, wherein said adjustment means further comprises:
      a. at least two attachment arms mounted generally perpendicular to the analytical chamber outer surface on opposing sides thereof;
      b. a leg mounted generally perpendicular to each said attachment arm, with said leg comprising first and second segments;
      c. means permitting the first segment of each said leg to be moved in a first direction perpendicular to said attachment arm;
      d. said means also permitting said first segment to be moved in a second direction perpendicular to said attachment arm and in opposition to said first direction; and
      e. joining means joining said first and second leg segments, said means comprising a locking universal joint to permit the angle between said first and second leg segments to be widely varied, and to lock said segments in position when said angle has been set.

2. The compact and portable electrochemical cell of claim 1 wherein said securing means further comprises suction cups mounted to said second leg segments at the end thereof opposite to said joining means.

3. A compact and portable electrochemical cell for making electrochemical measurements on the surface of a substrate of indefinite size comprising:
   a. an analytical chamber comprising a counter electrode and having a top and a bottom end;
   b. sealing means associated with the bottom end of said chamber to seal said bottom end to one surface of a substrate of indefinite size;
   c. a base plate, with said analytical chamber being mounted within said base plate;

d. means to mount a reference electrode in said base plate and near said analytical chamber;
e. an electrolyte fluid tank mounted to said base plate and in fluidic contact with said analytical chamber and said reference electrode;
f. securing means mounted to said base plate to removably and nondestructively secure said bottom end of said analytical chamber against one surface of a substrate of indefinite size, said securing means further comprising means to bias said analytical chamber towards the surface of a substrate of indefinite size in order to compress said sealing means and seal said analytical chamber to the surface of a substrate of indefinite size;
g. said adjustment means further comprising at least two leg base mounts mounted generally perpendicular to said base plate on opposing sides thereof;
h. mounting means mounting a suction cup assembly on each said leg base mount;
i. said mounting means comprising a screw with an associated adjustment nut attached to said leg base mount; wherein said screw and said adjustment nut permit said suction cup assembly to be moved towards or away from a substrate of indefinite size; and,
j. wherein said suction cup assembly comprises a bellows-type pneumatic suction cup.

4. The compact and portable electrochemical cell of claim 3 wherein said electrolyte fluid tank is mounted to said base plate at a slight angle to the vertical.

5. The compact and portable electrochemical cell of claim 4 wherein said slight angle is approximately 10 degrees.

6. The compact and portable electrochemical cell of claim 3 further comprising a first gas venting means in fluidic contact with said top end of said analytical chamber.

7. The compact and portable electrochemical cell of claim 3 further comprising a second gas venting means mounted on said electrolyte fluid tank.

8. A compact and portable electrochemical cell for making electrochemical measurements on the surface of a substrate of indefinite size comprising:
a. an analytical chamber comprising a counter electrode and having a top and a bottom end;
b. sealing means associated with the bottom end of said chamber to seal said bottom end to one surface of a substrate of indefinite size;
c. a first temperature control means mounted to the outside surface of said analytical chamber;
d. a base plate, with said analytical chamber being mounted within said base plate;
e. a second temperature control means mounted beneath said base plate and surrounding said bottom end of said analytical chamber;
f. means to mount a reference electrode in said base plate and near said analytical chamber;
g. an electrolyte fluid tank mounted to said base plate and in fluidic contact with said analytical chamber and said reference electrode; and
h. securing means mounted to said base plate to removably and nondestructively secure said bottom end of said analytical chamber against one surface of a substrate of indefinite size, said securing means further comprising adjustment means to adjust the distance between said analytical chamber and one surface of a substrate of indefinite size in order to bias said analytical chamber towards the surface of a substrate of indefinite size.

9. The compact and portable electrochemical cell of claim 8 wherein said electrolyte fluid tank is mounted to said base plate at a slight angle to the vertical.

10. The compact and portable electrochemical cell of claim 9 wherein said angle is approximately 10 degrees.

11. The compact and portable electrochemical cell of claim 8 further comprising a first gas venting means in fluidic contact with said top end of said analytical chamber.

12. The compact and portable electrochemical cell of claim 8 further comprising a second gas venting means mounted on said electrolyte fluid tank.

13. A compact and portable electrochemical cell for making electrochemical measurements on the surface of a substrate of indefinite size comprising:
a. an analytical chamber comprising a counter electrode and having a top and a bottom end;
b. sealing means associated with the bottom end of said chamber to seal said bottom end to one surface of a substrate of indefinite size;
c. a first temperature control means mounted to the outside surface of said analytical chamber;
d. a base plate, with said analytical chamber being mounted within said base plate;
e. means to mount a reference electrode in said base plate and near said analytical chamber;
f. an electrolyte fluid tank mounted to said base plate and in fluidic contact with said analytical chamber and said reference electrode;
g. securing means mounted to said base plate to removably and nondestructively secure said bottom end of said analytical chamber against one surface of a substrate of indefinite size, said securing means further comprising adjustment means to adjust the distance between said analytical chamber and one surface of a substrate of indefinite size in order to bias said analytical chamber towards the surface of a substrate of indefinite size; and,
h. wherein said securing means further comprises at least two independently adjustable mounting means to adjust the distance between said analytical chamber and one surface of a substrate of indefinite size in order to bias said analytical chamber towards the surface of a substrate of indefinite size, to permit electrochemical measurements on non-planar surfaces.

14. The compact and portable electrochemical cell of claim 13 wherein said electrolyte fluid tank is mounted to said base plate at a slight angle to the vertical.

15. The compact and portable electrochemical cell of claim 14 wherein said angle is approximately 10 degrees.

16. The compact and portable electrochemical cell of claim 13 further comprising a first gas venting means in fluidic contact with said top end of said analytical chamber.

17. The compact and portable electrochemical cell of claim 13 further comprising a second gas venting means mounted on said electrolyte fluid tank.

18. A compact and portable electrochemical cell for making electrochemical measurements on the surface of a substrate of indefinite size comprising:
a. an analytical chamber comprising a counter electrode and having a top and a bottom end;
b. sealing means associated with the bottom end of said chamber to seal said bottom end to one surface of a substrate of indefinite size;
c. a base plate, with said analytical chamber being mounted within said base plate;

d. a first temperature control means mounted beneath said base plate and surrounding said bottom end of said analytical chamber;

e. means to mount a reference electrode in said base plate and near said analytical chamber;

f. an electrolyte fluid tank mounted to said base plate and in fluidic contact with said analytical chamber and said reference electrode;

g. securing means mounted to said base plate to removably and nondestructively secure said bottom end of said analytical chamber against one surface of a substrate of indefinite size, said securing means further comprising adjustment means to adjust the distance between said analytical chamber and one surface of a substrate of indefinite size in order to bias said analytical chamber towards the surface of a substrate of indefinite size; and, h. wherein said securing means further comprises at least two independently adjustable mounting means to adjust the distance between said analytical chamber and one surface of a substrate of indefinite size in order to bias said analytical chamber towards the surface of a substrate of indefinite size, to permit electrochemical measurements on non-planar surfaces.

19. The compact and portable electrochemical cell of claim 18 wherein said electrolyte fluid tank is mounted to said base plate at a slight angle to the vertical.

20. The compact and portable electrochemical cell of claim 19 wherein said angle is approximately 10 degrees.

21. The compact and portable electrochemical cell of claim 18 further comprising a first gas venting means in fluidic contact with said top end of said analytical chamber.

22. The compact and portable electrochemical cell of claim 18 further comprising a second gas venting means mounted on said electrolyte fluid tank.

* * * * *